United States Patent
Hu et al.

(10) Patent No.: US 8,241,895 B2
(45) Date of Patent: *Aug. 14, 2012

(54) METHODS OF ALGAL GROWTH IN PHOTOBIOREACTORS

(75) Inventors: Qiang Hu, Chandler, AZ (US); Milton Sommerfeld, Chandler, AZ (US)

(73) Assignee: The Arizona Board of Regents, A Body Corporate Acting on Behalf of Arizona State University, Tempe, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/273,161

(22) Filed: Oct. 13, 2011

(65) Prior Publication Data

US 2012/0107918 A1    May 3, 2012

Related U.S. Application Data

(63) Continuation of application No. 12/280,338, filed as application No. PCT/US2007/004351 on Feb. 20, 2007.

(60) Provisional application No. 60/775,174, filed on Feb. 21, 2006, provisional application No. 60/799,930, filed on May 12, 2006.

(51) Int. Cl.
C12M 1/00 (2006.01)
C12M 1/36 (2006.01)
A01G 7/00 (2006.01)
C12N 1/12 (2006.01)

(52) U.S. Cl. ............... 435/292.1; 435/257.1; 435/286.5; 435/286.6

(58) Field of Classification Search ............... 435/292.1; 47/1.4
See application file for complete search history.

(56) References Cited

U.S. PATENT DOCUMENTS

| | | | |
|---|---|---|---|
| 1,046,813 A | 12/1912 | Laugenour | |
| 5,360,730 A * | 11/1994 | Orndorff et al. ............ | 435/257.1 |
| 6,391,638 B1 | 5/2002 | Shaaltiel | |
| 2004/0048364 A1 | 3/2004 | Trosch | |
| 2007/0092962 A1* | 4/2007 | Sheppard ...................... | 435/266 |
| 2010/0028976 A1 | 2/2010 | Hu et al. | |

FOREIGN PATENT DOCUMENTS

| | | |
|---|---|---|
| FR | 2662705 A2 | 6/1990 |
| JP | 61146182 A | 7/1986 |
| WO | WO-9105849 A1 | 5/1991 |
| WO | WO-2005/006838 A2 | 1/2005 |

OTHER PUBLICATIONS

Chaumont D. (1993) Biotechnology of algal biomass production: a review of systems for outdoor mass culture. J Appl Phycol 5: 593-604.
Chaumont, D. et al. (1988) Scaling up a tubular photobioreactor for continuous culture of *Porphyridium cruentum*—from laboratory to pilot plant, pp. 199-208. In Stadler T, Morillon J, Verdus MS, Karamanos W, Morvan H, Christiaen D (eds.), *Algal Biotechnology*, Elsevier Applied Science, London.

(Continued)

*Primary Examiner* — William H Beisner
(74) *Attorney, Agent, or Firm* — Tom Gallegos, Esq.; Justin Kniep, Esq.; Colleen Superko, Esq.

(57) ABSTRACT

The present invention provides novel photobioreactors, modules thereof, and methods for use in culturing and harvesting algae and cyanobacteria.

5 Claims, 22 Drawing Sheets

OTHER PUBLICATIONS

Cornwell, D.A. (1990). Air Stripping and Aeration, in Water Quality and Treatment, McGraw Hill Inc., New York, p. 229-268.

Fernandez, F.G., et al. (1998). Modeling of biomass productivity in tubular photobioreactors for microalgal cultures: effects of diluation rate, tube diameter, and solar irradiance, *Biotech. and Bioeng.*, 58:6:605-616.

Gitelson A., Hu Q. and Richmond A. (1996) Photic volume in photobioreactors supporting ultrahigh population densities of the photoautotroph *Spirulina platensis*. Applied and Environmental Microbiology 62: 1570-1573.

Gudin C. and Chaumont D. (1991) Cell fragility—the key problem of microalgae mass production in closed photobioreactors. *Bioresource Technol*. 38: 145-151.

Hu Q. 2004. Industrial production of microalgal cell-mass and secondary products—major industrial species: *Arthrospira (Spirulina) platensis*. pp. 264-272. In: Richmond A. (ed.) Handbook of microalgal culture: biotechnology and applied Phycology, Blackwell Science Ltd., Oxford, UK.

Hu Q. and Richmond A. (1994) Optimizing the population density of *Isochrysis galbana* grown outdoors in a glass column photobioreactor. Journal of Applied Phycology 6 : 391-396.

Hu Q., Faiman D. and Richmond A. (1998) Optimal tilt angles of enclosed reactors for growing photoautotrophic microorganisms outdoors. Journal of Fermentation and Biotechnology 85: 230-236.

Hu Q., Guterman H. and Richmond A. (1996) A flat inclined modular photobioreactor (FIMP) for outdoor mass cultivation of photoautotrophs. Biotechnology and Bioengineering 51: 51-60.

Hu Q., Guterman H. and Richmond A. (1996) Physiological characteristics of *Spirulina platensis* cultured at ultrahigh cell densities. Journal of Phycology 32: 1066-1073.

Hu Q., Kurano N., Iwasaki I., Kawachi M. and Miyachi S. (1998) Ultrahigh cell density culture of a marine green alga, *Chlorococcum littorale* in a flat plate photobioreactor. Applied Microbiology and Biotechnology 49: 655-662.

Hu Q., Yair Z. and Richmond A. (1998) Combined effects of light intensity, light-path and culture density on output rate of *Spirulina platensis* (Cyanobacteria). European Journal of Phycology 33: 165-171.

Hu, et al., "A Flat Inclined Modular Photobioreactor for Outdoor Mass Cultivation of Photoautotrophs," Biotechnology and Bioengineering, vol. 51, No. 1, Jul. 1996, pp. 51-60.

Iwasaki I., Hu Q., Kurano N. and Miyachi S. (1988) Effect of extremely high-$CO_2$ stress on energy distribution between photosystem I and photosystem II in a 'High-$CO_2$' tolerant green alga, *Chlorococcum littorale* and the intolerant green Alga *Stichococcus bacillaris*. Journal of Photochemistry and Photobiology B: Biology 44/3: 184-190.

Lee Y.K. (1986) Enclosed bioreactor for the mass cultivation of photosynthetic microorganism: the future trend. *Trends Biotechnol.* 4: 186-189.

Lee Y.K., Ding S.Y., Low C.S. and Chang Y.C. (1995) Design and performance of an ?-type tubular photobioreactor for mass cultivation of microalgae. J. Appl. Phycol 7:47-51.

Pirt S.J., Lee Y.K., Walach M.R., Pirt M.W., Balyuzi H.H.M. and Bazin M.J. (1983) A tubular bioreactor for photosynthetic production of biomass from carbon dioxide: design and performance. *J. Chem. Tech. Biotechnol*. 33: 35-58.

Ramos de Ortega and Roux J.C. (1986) Production of *Chlorella* biomass in different types of flat bioreactors in temperate zones. *Biomass* 10: 141-156.

Richmond A. (1990) Large scale microalgal culture and applications. In: Round/Chapman (eds) Progress in Phycological Research Biopress, London, 7: 1-62.

Richmond A. (1992) Open systems for mass production of photoautotrophic microalgae outdoors: physiological principles. *J. Appl. Phycol*. 4: 281-286.

Richmond A. and Hu Q. (1997) Principles for utilization of light for mass production of photoautotrophic microorganisms. Applied Biochemistry and Biotechnology. 63-65: 649-658.

Richmond A., Boussiba S., Vonshak A. and Kopel R. (1993) A new tubular reactor for mass production of microalgae outdoors. *J. Appl. Phycol*. 5: 327-332.

Samson R & Leduy A (1985) Multistage continuous cultivation of blue-green alga *Spirulina maxima* in the flat tank photobioreactors with recycle. *Can. J. Chem. Eng*. 63: 105-112.

Silva, H.J., Cortinas T. and Ertola R.J. 1987. Effect of hydrodynamic stress on *Dunaliella* growth. *J. Chem. Tech. Biotechnol*. 40: 253-264.

Tamiya H. (1957) Mass culture of algae. *Ann Rev. Plant Physiol*. 8: 309-334.

Torzillo G., Carlozzi P., Pusharaj B., Montani E. and Materassi R. (1994) A two-plane tubular photobioreactor for outdoor culture of *Spirulina. Biotechnol. Bioeng*. 42: 891-898.

Tredici M. (2004) Mass production of microalgae: photobioreactors, pp. 178-214. In: Richmond A. (ed.) Handbook of microalgal culture: biotechnology and applied Phycology, Blackwell Science Ltd., Oxford, UK.

Tredici M.R. and Materassi R. (1992) From open ponds to vertical alveolar panels: the Italian experience in the development of reactors for the mass cultivation of photoautotrophic microorganisms. *J. Appl. Phycol*. 4: 221-31.

Tredici M.R., Carlozzi P., Zittelli G.C. and Materassi R. (1991) A vertical alveolar panel (VAP) for outdoor mass cultivation of microalgae and Cyanobacteria. *Bioresource Technol*. 38: 153-159.

Watanabe Y., Joel de la Noue. and Hall D.O. (1995) Photosynthetic performance of a helical tubular photobioreactor incorporating the cyanobacterium *Spirulina platensis*. Biotechnol Bioeng 47: 261-269.

Xiu, Z-L, Zeng, A-P, Deckwer, W-D (1998). Multiplicity and stability analysis of microorganisms in continuous culture: effects of metabolic overflow and growth inhibition, *Biotechnology and Bioeng.*, 57:3:251-261.

\* cited by examiner

METHODS OF ALGAL GROWTH IN PHOTOBIOREACTORS

CROSS REFERENCE

This application is a continuation of U.S. patent application Ser. No. 12/280,338, filed Aug. 17, 2009, which in turn is the National Stage under 35 U.S.C. §371 of International Application No. PCT/US2007/004351, filed Feb. 20, 2007, which claims the benefit of priority of U.S. Provisional Patent Application Nos. 60/775,174, filed Feb. 21, 2006 and 60/799,930, filed May 12, 2006, each of which is incorporated herein by reference.

BACKGROUND OF THE INVENTION

Microalgae and cyanobacteria (for short, algae) are microplants and require mostly simple mineral nutrients for growth and reproduction. By utilizing photon energy, such as sunlight and artificial illumination, algae convert, through photosynthesis, water and carbon dioxide into high-value organic compounds (e.g., pigments, proteins, fatty acids, carbohydrates, and secondary metabolites). Algae exhibit a growth potential an order of magnitude greater than higher plants because of their extraordinarily efficient light and nutrient utilization.

With over 40,000 identified species, algae represent a very diverse group of organisms. They naturally produce many novel, as yet largely untapped classes of bioproducts. Globally, annual sales of algae-derived products (pharmaceuticals, nutraceuticals, agrochemicals, human food, and animal feed) were estimated to be $2 billion in 2004. By taking advantage of the latest breakthroughs in molecular biology, metabolic engineering and functional genome research, algae can serve as an excellent gene-expression vehicle for production of recombinant proteins and other biologically active compounds for human and animal health and nutrition.

Due to the ability to rapidly uptake nutrients (such as carbon dioxide, nitrogen, and phosphorous) from the surrounding environment and convert them into organic compounds such as proteins stored in the cell, algae have been proposed and tested in natural and engineered systems to remove and recycle waste nutrients from wastewater and carbon dioxide-rich flue gases emitted from fossil fuel-fired power generators. The algal biomass produced as a by-product of the bioremediation process can then be used as feedstock for production of biofuels (such as biodiesel, ethanol, or methane), animal feed additives, and organic fertilizer.

Although application of algae for renewable biofuels of both liquid and gaseous forms and high-value products, and for environmental bioremediation is scientifically and environmentally sound, economic viability of algal applications is determined by the efficiency and cost-effectiveness of industrial-scale culture vessels, or so-called photobioreactors (for short, reactors), in which algal grow and proliferate.

Industrial photobioreactors currently are commonly designed as open raceways, i.e. shallow ponds (water level ca. 15 to 30 cm high) each covering an area of 1000 to 5000 $m^2$ constructed as a loop in which the culture is circulated by a paddle-wheel (Richmond, 1986). This production mode has the advantage of being relatively simple in construction and maintenance, but it has many disadvantages which relate to the factors controlling productivity of algal grown outdoors (Richmond, 1992; Tredici et al. 1991). The overall low productivity of the open raceways is due mainly to the lack of temperature control and the long light-path, as well as poor mixing. The open raceways in which the algal culture is open to the air is also responsible for culture contamination with airborne microorganisms and dusts, often causing culture failure or crashes. The significant drawbacks of the open raceways have prompted the development of closed systems, i.e. photobioreactors made of transparent tubes or containers in which the culture is mixed by either a pump or air bubbling (Lee 1986; Chaumont 1993; Richmond 1990; Tredici 2004).

A number of tubular photobioreactors have been proposed and developed since the pioneering works of Tamiya et al. (1953) and Pirt et al. (1983). These solar receptor bioreactors are generally serpentine or helical in form, made of glass or plastic with a gas exchange vessel where $CO_2$ and nutrients are added and $O_2$ removed connected to the two ends of the tubing, and with recirculation of the culture between the vessel and tubing performed by a pump (Gudin and Chaumont 1983) or an air-lift (Pirt et al. 1983; Chaumont et al. 1988; Richmond et al. 1993). Because of their improvement in light path, culture temperature, and mixing, tubular photobioreactors not only increase considerably algal biomass productivity, but also enable more algal species of commercial interest to grow and proliferate under more controllable culture conditions.

On the other hand, the tubular-type photobioreactors suffer from their own inherit problems. First of all, tubular photobioreactors have a significant 'dark zone or dark volume' (usually consisting of 10-15% of the total culture volume) associated with a degas reservoir/tank where the exchange of excess amounts of dissolved oxygen with carbon dioxide occur. Algal cells entering the dark zone cannot perform photosynthesis, but consume, through cellular respiration, cell mass which have previously been assimilated under light. As a result, a tubular reactor will only sustain biomass yield of 85-90% of the theoretical maximum. Secondly, tubular photobioreactors have the potential to accumulate in the culture suspension high concentrations of molecular oxygen evolved from photosynthesis, which in turn inhibits photosynthesis and thus biomass production potential. Thirdly, mechanic pumps that are commonly employed by tubular photobioreactors to facilitate culture mixing and circulation within long tubes can cause serious cell damage. For example, some 15% of the damage to cells has been reported to be associated with operation of tubular-type bioreactors (Shilva et al. 1987). Gudin and Chaumont (1991) also observed that significant cell fragility occurred in a *Haematococcus* culture maintained in a large-scale tubular photobioreactor. Due to severe hydrodynamic stress created by various mechanical pumps, only a limited number of algal species are able to survive in a tubular bioreactor. Also, the high capital and maintenance costs associated with tubular photobioreactors have limited their applications only for production of small quantity, high-value specialty products.

During the last ten years, however, attention has focused on flat plate-type photobioreactors. This type of reactor was first described by Samson and Leduy (1985) and by Ramos de Ortega and Roux (1986), and further refined by Tredici et al. (1991, 1997) and Hu et al. (1996, 1998a,b). Flat plate-type designs offer greater advantages over the tubular-type systems: 1) no "dark zone" is associated with the flat-plate design and the reactors are illuminated in their entirety, thus boosting photosynthetic productivity; 2) aeration that facilitates culture mixing and turbulence exerts little harm to algal cells because of the minimum hydrodynamic force created by air bubbling; 3) harmful levels of oxygen are not built up in flat plate-type system because of their short reactor heights (i.e., 3 to 10 feet); 4) flat-plate reactors can be set at various orientations and/or tilted angles aimed at maximal exposure to solar energy throughout the year to further enhance photosynthetic biomass yield; and 5) compared to tubular reactors, flat-plate reactors require considerably less capital and maintenance costs.

However, application of flat plate-type reactors has encountered a major engineering obstacle, i.e., difficulty of scaling up the flat plat-type design to a commercial level. Therefore, flat plate reactors have only been used as benchtop culture devices and as small outdoor culture units for study of algal growth physiology, and have never been applied to industrial cultivation of algae.

SUMMARY OF THE INVENTION

In one aspect, the present invention provides photobioreactors, comprising:
 (a) a container adapted for holding fluid, comprising
  (i) opposing first and second sidewalls, wherein at least one of the first and second sidewalls is transparent;
  (ii) opposing first and second endwalls;
  (iii) a container bottom; and
  (iv) a container cover,
  wherein the first and second sidewalls comprise a plurality of separate sections, and wherein the separate sections are in fluid communication;
 (b) support struts for connecting the plurality of separate sections of the first and second sidewalls;
 (c) at least one inlet port in fluid communication with the container;
 (d) at least one outlet port in fluid communication with container;
 (e) an aeration system in fluid communication with the container; and
 (f) a temperature control system connected to the container so as to control temperature of fluid within the container.

In one preferred embodiment, the photobioreactor further comprises one or more baffles connected to the first and second sidewalls, so as to form a barrier and to partially separate the container into multiple compartments.

In another embodiment, the invention provides photobioreactor modules, comprising two or more photobioreactors of the first aspect of the invention, wherein the containers of each photobioreactor are in fluid communication. Individual photobioreactor containers can also be set in parallel and the fluid from individual photobioreactor containers can be harvested through outlet ports connected to a common harvesting/draining manifold system.

In a second aspect, the present invention provides a photobioreactor panel unit, comprising:
 (a) a container adapted for holding fluid, comprising opposing first and second sidewalls and opposing first and second endwalls, wherein the container define an interior, a top opening and a bottom opening, wherein at least one of the first and second sidewalls is transparent, and wherein the first and second sidewalls are substantially flat;
 (b) a top cap that fits over the top opening of the panel body; and
 (c) a base cap that fits under the bottom opening of the panel body;
 one or both of the top cap and the bottom cap further comprise one or more channels, to provide fluid connection to a separate photobioreactor panel unit.

In a preferred embodiment, the photobioreactor panel unit further comprises one or more baffles extending between the first and second sidewalls, so that the interior comprises a plurality of compartments.

In another embodiment, the invention provides photobioreactor modules, comprising two or more photobioreactor panel units of the second aspect of the invention, wherein the container of each photobioreactor is in fluid communication with all other containers in the photobioreactor module.

In a third aspect, the present invention provides methods for making the photobioreactors of the first or second aspect of the invention, comprising assembling the photobioreactor of the first or second aspect of the invention from their component parts.

In a fourth aspect, the present invention provides methods for algal growth, comprising incubating algae in a growth medium in a photobioreactor of the first or second aspect of the invention, and exposing the algae to light. In a preferred embodiment, the method further comprises harvesting the algal cells. In a further preferred embodiment, the method comprises isolating biological products from the harvested algal cells. In a further embodiment, the methods for growing algae comprise incubating the algae in the presence of a nutrient source selected from the group consisting of wastewater from concentrated animal feeding operations, agriculture runoff water, underground saline water, industrial wastewater, domestic wastewater, contaminated groundwater, waste gases emitted from power generators, and flue gas emissions from fossil fuel fired power plants.

DESCRIPTION OF THE INVENTION

In a first aspect, the present invention provides a photobioreactor comprising:
(a) a container adapted for holding fluid, comprising
(i) opposing first and second sidewalls, wherein at least one of the first and second sidewalls is transparent;
(ii) opposing first and second endwalls;
(iii) a container bottom; and
(iv) a container cover,
wherein the first and second sidewalls comprise a plurality of separate sections, and wherein the separate sections are in fluid communication;
(b) support struts for connecting the plurality of separate sections of the first and second sidewalls;
(c) at least one inlet port in fluid communication with the container;
(d) at least one outlet port in fluid communication with container;
(e) an aeration system in fluid communication with the container; and
(f) a temperature control system connected to the container so as to control temperature of fluid within the container.

The photobioreactor of this first aspect of the invention can be expanded as desired through the use of the sidewall sections and struts, to produce an industrially useful flat panel photobioreactor, as described in more detail below, fulfilling a great need in the art.

The photobioreactors of the present invention, and modules comprising a plurality of such photobioreactors, are designed to sustain high performance of mass cultivation of algae, particularly using solar radiation, for commercial production of, for example, renewable biofuels and other value-added products, as well as for bioremediation of, for example, wastestreams of industrial, agriculture, and domestic origin.

As used herein, the term "in fluid communication with" means a connection that permits the passage of liquids or gases between the recited components.

Figure 1:
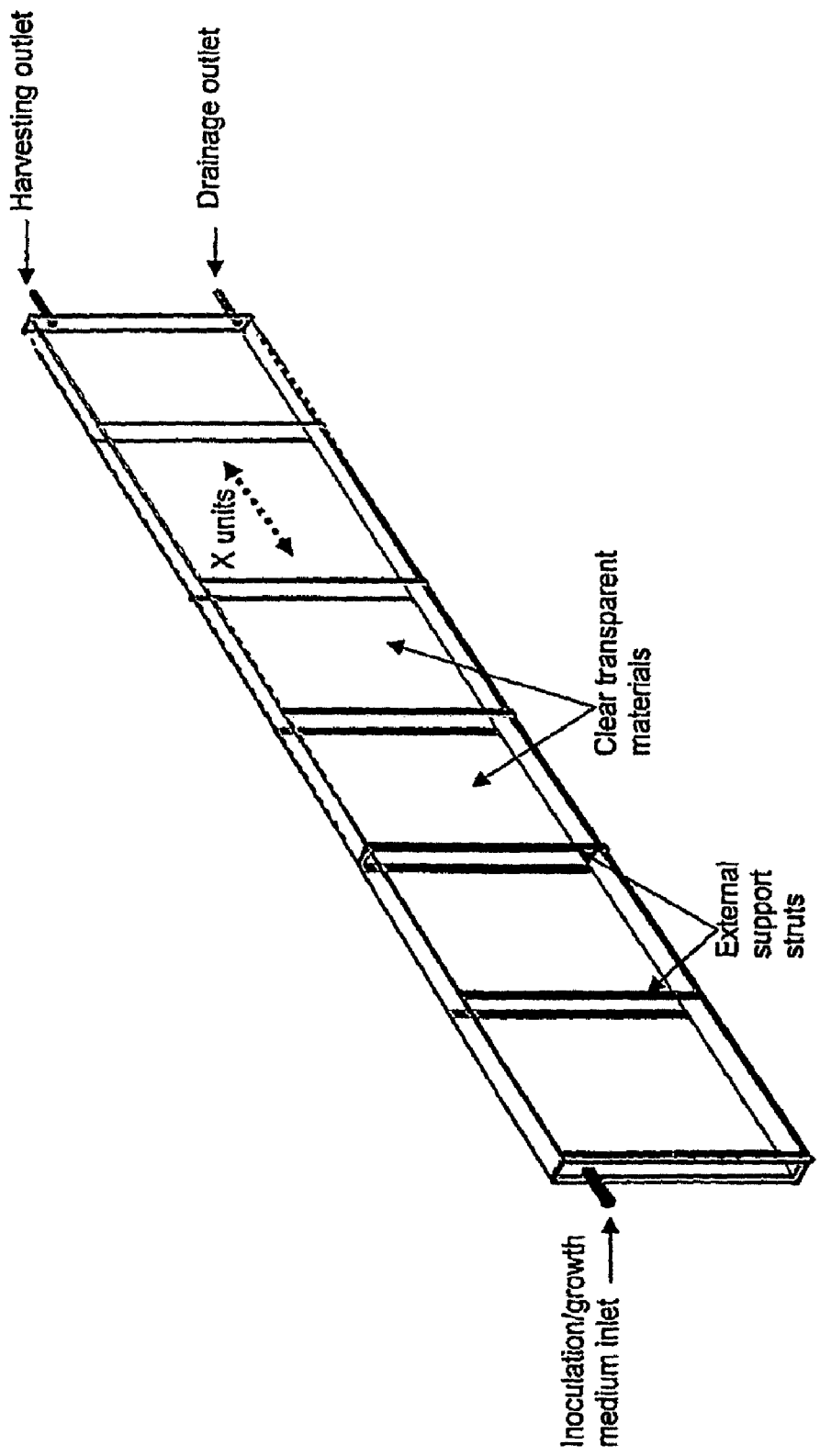
FIG. 1. An exemplary geometric configuration of the reactor. Clear transparent materials can be glass, or rigid/flexible plastic (e.g., polycarbonates, PVC, acrylic, polyethylene).

A schematic drawing of an exemplary photobioreactor of this first aspect of the invention is shown in FIG. 1.

At least one of the first and second sidewalls of the container is transparent. In embodiments where only one of the sidewalls is transparent, that is the sidewall that will face the sun when the photobioreactor is used for algal growth outdoors. Transparent sidewalls of the container can be made of any transparent material including, but not limited to, glass or plastic plates. Plastic sidewalls can be made of materials including, but not limited to, PVC, polycarbonate, acrylic, or polyethylene. Non-transparent sidewalls can be made of any suitable material, including but not limited to plastic (such as PVC, polycarbonate, acrylic, or polyethylene), fiberglass, stainless steel, concrete, and plastic liners. Such non-transparent sidewalls can be used as the sidewall facing away from the sun when the photobioreactor is used for algal growth outdoors.

As used herein, the term "plurality" means two or more; thus, the sidewalls comprise at least two separate sections. The transparent sidewall that will face the sun ("front sidewall") comprises a plurality of sections, while the "back sidewall" (which can be transparent or non-transparent) can be a single section along the length of the photobioreactor, or can also comprise a plurality of sections.

The distance between the inner sides of the two sidewalls is the "light path," which affects sustainable algal concentration, photosynthetic efficiency, and biomass productivity. The light path can be between approximately 5 millimeters and 40 centimeters; preferably between 100 millimeters and 30 centimeters, more preferably between 50 millimeters and 20 centimeters, even more preferably between 1 centimeter and 15 centimeters, and most preferably between 2 centimeters and 10 centimeters. The most optimal light path for a given application will depend, at least in part, on factors including the specific algal species/strains to be grown and/or specific desired product/s to be produced.

The height of reactor sidewalls can range from 2 feet to 8 feet or more, depending on the type and thickness of sidewall materials used and economic considerations. For example, the higher the sidewall, the thicker the wall material required, and the higher the material cost. Alternatively, while low sidewalls save on material costs, an increased number of separate sidewall sections are required to meet a given total volume requirement; in addition, an increased number and/or more complex system of inlet ports, outlet ports, aeration systems, and temperature control systems would be required.

So, for each individual application, the height of the sidewall is optimized from both engineering and economic perspectives.

In one embodiment, the sidewalls and endwalls are substantially flat; this embodiment is preferred when using glass, rigid plastic sheets, stainless steel or concrete to construct the sidewalls and endwalls. In other embodiments, particularly where the sidewalls and/or endwalls are made of flexible plastic sheets, which are supported by external struts, the sidewalls may have some curvature imposed by individual struts.

The photobioreactor of this first aspect of the invention can range in length from one meter to hundreds of meters. Due to the design features of the present photobioreactor, the sidewalls can be of any length.

The heights of the face (front) sidewall and back sidewall can be the same or slightly different. For example, the front sidewall can be slightly shorter than the back sidewall in embodiments where the photobioreactor is designed to incline to a certain angle toward the sun (for maximizing solar energy harvesting for algal photosynthesis; see below).

The front sidewall can be made of the same or different clear materials from the back sidewall, with optimization based on cost-saving, maximum light penetration capacity, and heat mass transfer efficiency. For example, in a cold weather region, reactor sidewalls made of plastic may provide an advantage over glass plates because the plastic material may reduce heat loss from culture suspension to the surroundings. Alternatively, glass has a higher heat transfer efficiency, and thus the use of glass sheets as the front and/or back sidewalls will allow the reactor to dissipate access solar-heat more efficiently than a plastic sidewall material in a warmer climate region.

In another example, if one clear material is more transparent and/or able to maintain high transparency longer than another type of material, but the latter is less expensive, then the higher quality material may be used for front sidewall whereas the cheaper material may be used for the back sidewall. Further cost reduction can be obtained by using back sidewalls that are not transparent and are made using lower cost and/or higher strength material, such as concrete, stainless steel, plastic liners placed on the top of an earth bank ("berm") of desired shape, and fiberglass.

In various preferred embodiments, the first and second sidewalls comprise 2, 3, 4, 5, 10, 25, 50, 75, 100, 150, 200, 500, or more separate sections. In these various embodiments, the front sidewall can comprise 2, 3, 4, 5, 10, 25, 50, 75, 100, 150, 200, 500, or more separate sections while the back sidewall can comprise a single section, or can also comprise 2, 3, 4, 5, 10, 25, 50, 75, 100, 150, 200, 500, or more separate sections. There is no upper limit on the number of separate sections that can be used, so long as appropriate struts are used. In a preferred embodiment, the number of support struts in the photobioreactor is n+1, wherein "n" is the number of sections of the first and/or second sidewalls.

The container bottom can be made of any material that can form a seal with the sidewalls to define an interior space of the container that can hold and retain an algal culture to be grown in the photobioreactor. Such materials include but are not limited to concrete, tile, glass, or thin sheet of plastic or stainless steel. There is no requirement that the container bottom be transparent, although it may be transparent. In a preferred embodiment, the container bottom is made of the same materials as one or both of the sidewalls and/or endwalls.

Figure 16A:
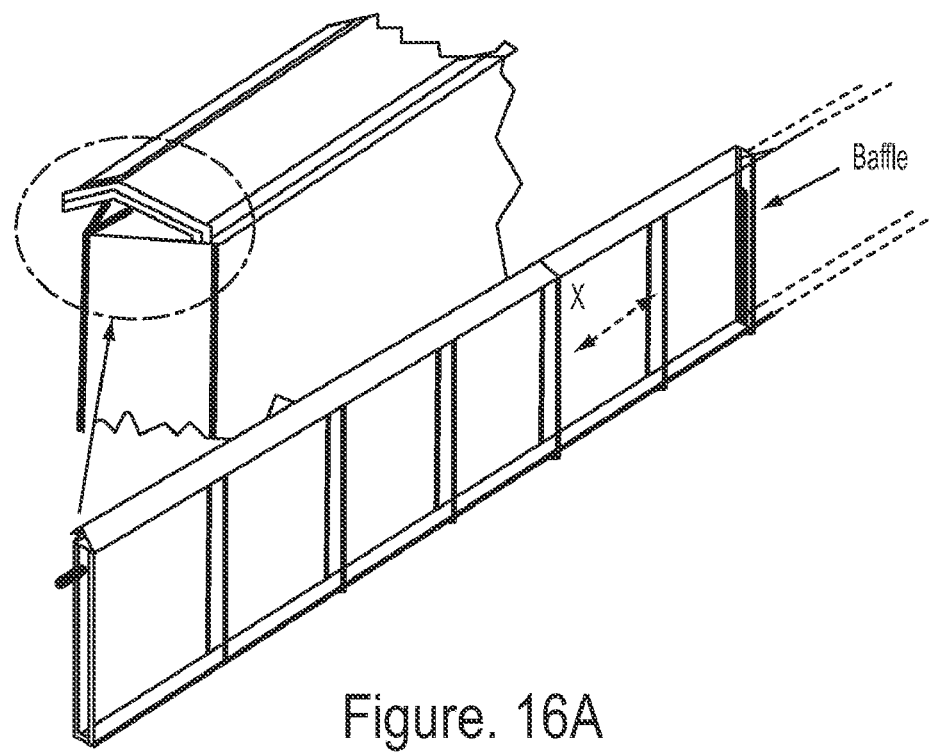
FIG. 16. Examples of reactor top covers. It is preferred to be transparent materials, such as glass or clear plastic.
Figure 16B:
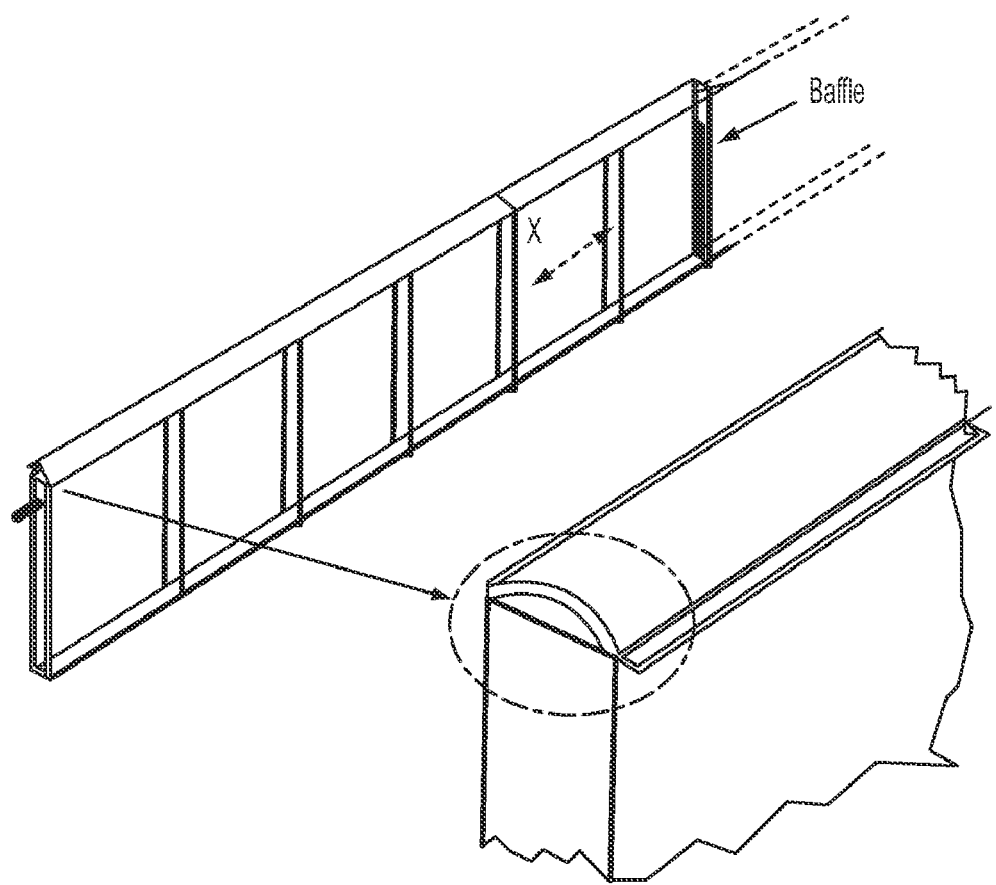

The photobioreactor also comprises a container top to prevent airborne-dusts/microbial organisms from entering the culture, and to prevent water evaporation. The top can be made of glass or plastic materials, and is preferred to be transparent to allow light penetration. (See, for example, FIG. 16) In a most preferred embodiment, the top is made of the same materials as the one or both of the sidewalls and/or endwalls. It is also preferred that the top be set at an angle to the horizon or has curvature. A cover with a tilted angle or curved shape will prevent accumulation of water drops with or without algal cells on the inner surface of the cover. Potential build up of water drops and/or growing algal cells on the inner surface of the cover will reduce light penetration into the culture. The cover is thus preferably designed such that it is easy to remove and reset to enable cleaning of reactor inner surface, as needed.

In this first aspect of the invention, support struts are used to provide a framework to connect the separate sections of the first and/or second sidewalls. The struts can be of any material suitable for this purpose, including but not limited to metal and high strength plastic, concrete, or ceramic. As discussed above, the struts can serve a support function, and also provide the surface area for sidewalls to join. Struts may also define the length of reactor light path (depth) and configuration of reactor unit (e.g., linear or serpentine shape). In general, the struts provide support and surface area for sidewalls to join or to have the sidewalls bonded onto the strut. The inner structure formed by sidewalls join one another and by the front and back sidewalls creates a single interior space in the container, which can be broken into compartments through the use of baffles, described more fully below.

Figure 17A:
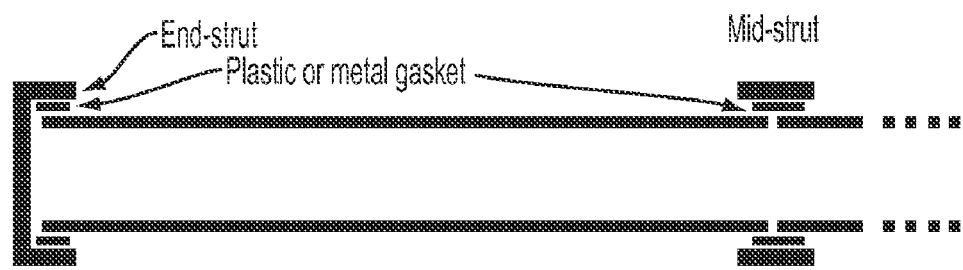
FIG. 17. Top—(A) and side-views (B) of end-strut. The end-strut can be made of, for example, stainless steel or plastic sheet.
Figure 17B:
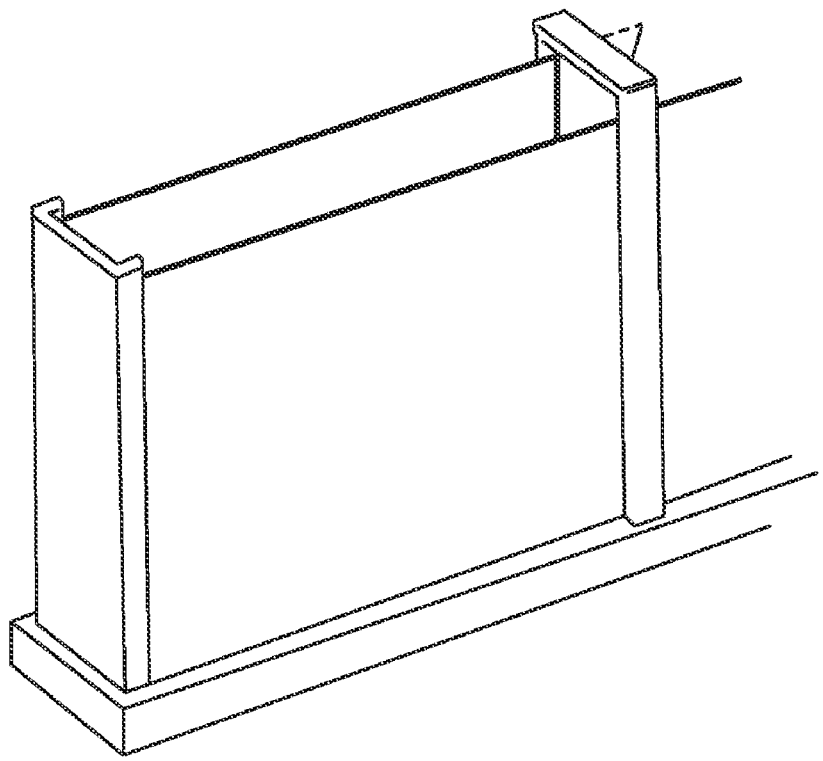
Figure 18A:
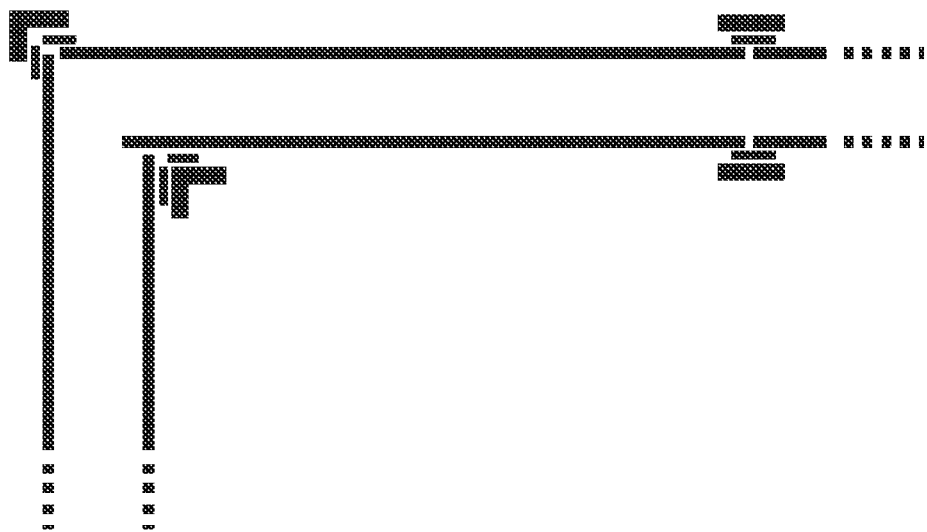
FIG. 18. Top—(A) and side-views (B) of corner-struts. The corner-struts can be made of, for example, metal or high-strength plastic materials.
Figure 18B:
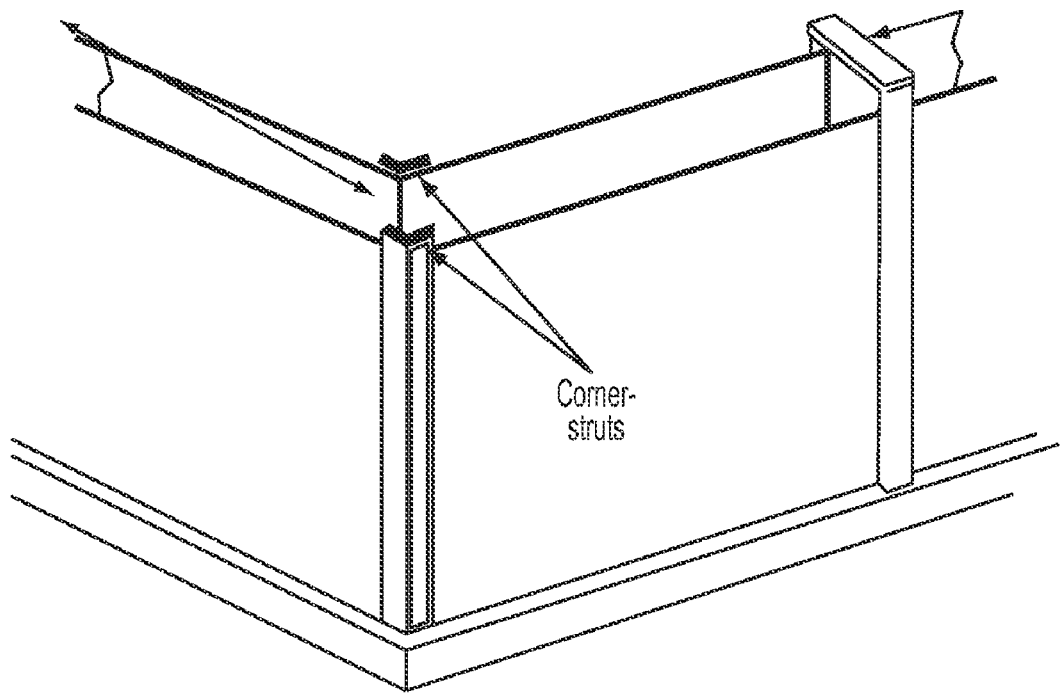

Struts are thus the means to join sidewalls piece by piece, side by side, which enable a single photobioreactor unit to have any length or configuration. Some struts may also provide frame structures for baffles to fix on them (see below) to create many inner-compartments within a single photobioreactor unit. Struts can also be used to provide support for endwalls in either linear or serpentine configurations, as well as corners (See FIGS. 17-18 for exemplary depictions of struts used to support endwalls or corners.)

In a preferred embodiment, the support struts are located external to the container and are arranged to provide support to hold the container and also to provide the surface for individual sidewalls to join.

In a preferred embodiment, for a given umber (n) of sidewalls, the number of struts including end-struts is 'n+1'.

Figure 19:
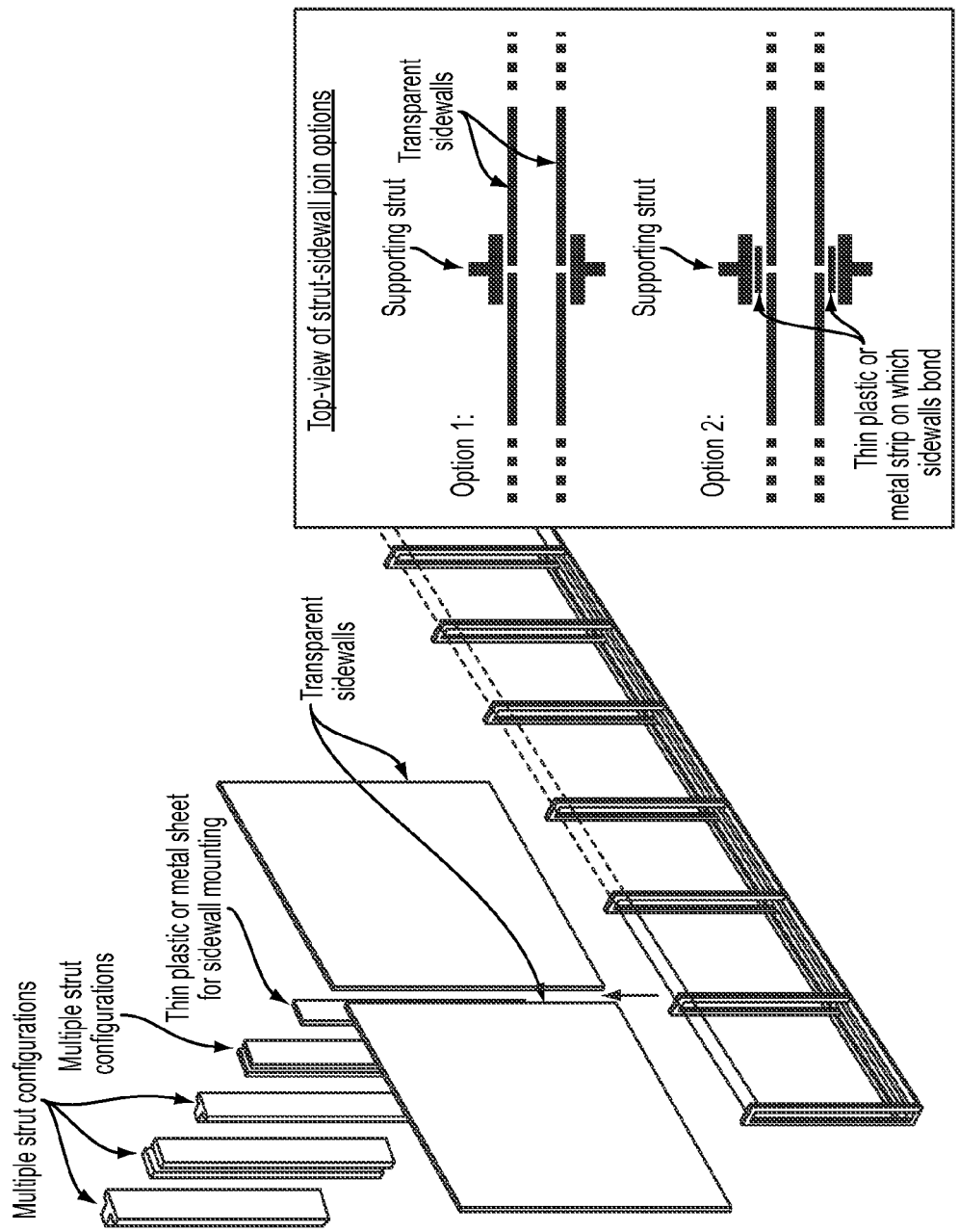
FIG. 19. Configurations of support struts. Struts can be made of, for example, metal, plastic, or concrete. Sidewalls can bound directly to the struts or to a thin strip of, for example, metal or plastic sheet. In the latter case, the strut only serves a supporting function.

There are a number of design options for providing support struts to connect the plurality of separate sections of the first and/or second sidewalls, including but not limited to:

The strut not only provides the surface area for the edges of two sidewalls to be bonded to it, but also to provide weight support from the external direction. In this embodiment, it is preferred that the surface of the strut is smooth and flat, and also compatible with the type of bonding agent (including but not limited to glue, silicone, epoxy, etc) used to join the sidewall material to the strut. See, for example, FIG. 19.

The strut serves as support and also provides a surface area for the edges of two sidewalls to contact. However, the sidewall is not bonded directly to the strut, but to a thin sheet of plastic or metal (e.g., a strip of thin plastic or stainless steel sheet of the same size of the strut's inner surface) inserted between the sidewalls and the strut. Since the strut is not directly contacted and bonded to the sidewalls, the nature of the strut material and/or quality of the inner surface of the strut becomes less critical. Also, in case a sidewall needs to be replaced, it can be easily removed from the strut structure. The sidewalls bonded to a high quality, thin plastic, or stainless steel strip ensures better sealing at the sidewall joining region. See, for example, FIG. 19.

A gasket (any suitable material, including rubber, plastic, or analogous materials) can be placed between the sidewall and inner surface of the strut or inner surface of a thin plastic or metal strip to prevent or reduce thermo-contraction/expansion due to temperature changes under outdoor conditions. For the same reason, the gasket will also be placed between the edge of the sidewall and base cap or bottom base of the reactor.

The type of bonding agent used depends on the type of materials used in sidewall construction and the strut design, as discussed above. Those of skill in the art will be able to optimize the type of bonding agent based on the teachings herein. Non-limiting examples of such bonding agents include, but are not limited to, various glues, epoxies, and silicone.

It will be apparent to those of skill in the art that many other such designs for strut support of the container sections could be implemented, based on the teachings herein.

The photobioreactors contain at least one inlet port in fluid communication with the container, for introducing fluid, including but not limited to culture medium, algal suspensions, water/wastewater, and nutrient solutions, into the container. In a preferred embodiment, the inlet port is located at an endwall of the photobioreactor, preferably near the top of the container. There can be one or more inlet ports located at or near the endwall to deliver culture medium, algal suspensions, water/wastewater, or nutrient solutions. Different solutions can also enter the reactor through a single inlet. The purpose of inlet/s located at or near the endwall is to create a nutrient gradient in which the highest nutrient concentration is near the inlet and the lowest concentration is at the far end of the reactor. Different nutrient concentrations affect the growth and biochemical composition of algal cells. For example, nutrient-rich medium may stimulate and sustain a high growth rate and biomass productivity, whereas nutrient depleted medium may stimulate biosynthesis and cellular accumulation of neutral lipids, long chain fatty acids, and/or secondary carotenoids. A nutrient gradient created in a reactor of this design thus allows a continuous shifting of algae from a high biomass production mode to a high accumulation of specific desired product mode. The outlet at or near the far end of the reactor will ensure harvesting algal cells of the highest content of desired compound/s/product/s in the cell.

Alternatively, multiple inlets ports may be located at certain distance apart from one another to ensure nutrient and/or algal cell concentrations to be more or less homogenous throughout the reactor unit. In this case, the cells grown in a given reactor unit or module will have identical, desirable physiological status for specific applications. In the case of a linear reactor unit, multiple inlet ports may be located along the reactor length, when desired as discussed above. The distance between inlets ports can be optimized for a given use.

The inlet port(s) can be located at any height relative to the sidewalls or struts. When multiple photobioreactor units are arranged in cascade and culture suspension flows from one reactor unit to next one at the downstream site, it is preferred to have the inlet port(s) near the top of the photobioreactor.

The photobioreactors of this first aspect of the invention comprise at least one outlet port in fluid communication with the container, for removing fluid from the container, including algal culture suspensions for harvesting. In a preferred embodiment, the outlet port is located at an opposite endwall of the photobioreactor from the inlet port. Placement of the outlet port is based on the specific needs of the user. For example, in using the overflow principle as a means of harvesting and culture level control, the outlet port is preferably placed near the top of the photobioreactor or the position where an ideal culture level can be maintained. In this embodiment, it is preferred to have the outlet port located at or near the far endwall (away from the inlet port). Alternatively, if harvesting is controlled by, for example, a solenoid valve-mediated outlet, then the outlet port is preferably placed near the bottom of the reactor. In this embodiment, the outlet port is designed such that it serves both for harvesting and reactor drainage. When the outlet port(s) is/are located near the top of the photobioreactor, a separate outlet near or at the bottom of the endwall is necessary for reactor drainage.

Figure 22:
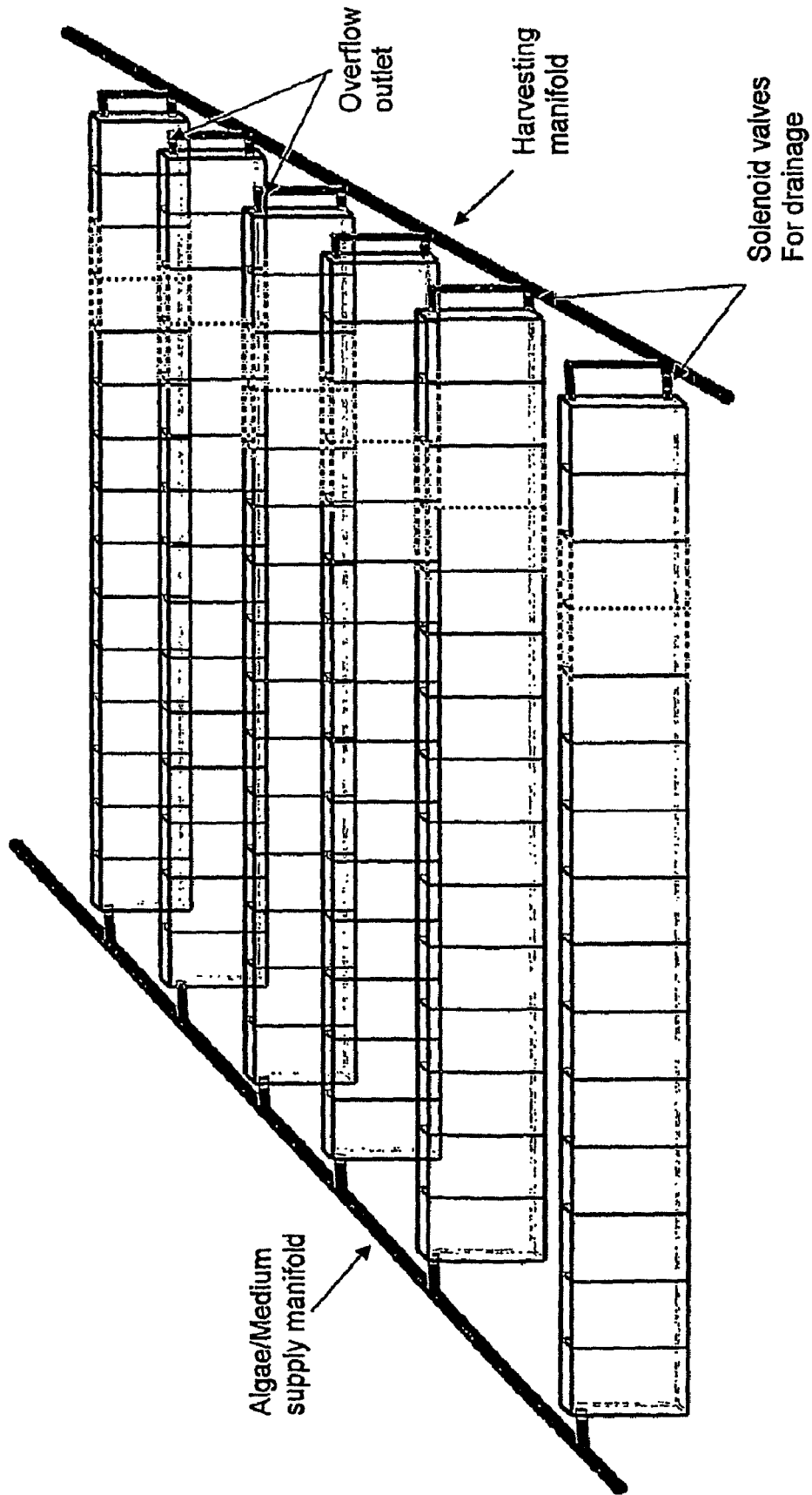
FIG. 22. Photobioreactor units an/or photobioreactor modules can be set up at the same level on the ground. Manifold systems are set for supply of growth medium/algae and harvesting and/or draining of algal culture from reactor units/modules.

For a single photobioreactor, it may not be critical to have the outlet at a particular location relative to the endwall. However, when multiple photobioreactors are to be arranged in parallel as a module, capital/maintenance costs of piping/connecting materials may be reduced if all the outlet ports are located at the endwalls and connected to a common manifold piping system (FIG. 22).

Figure 8:
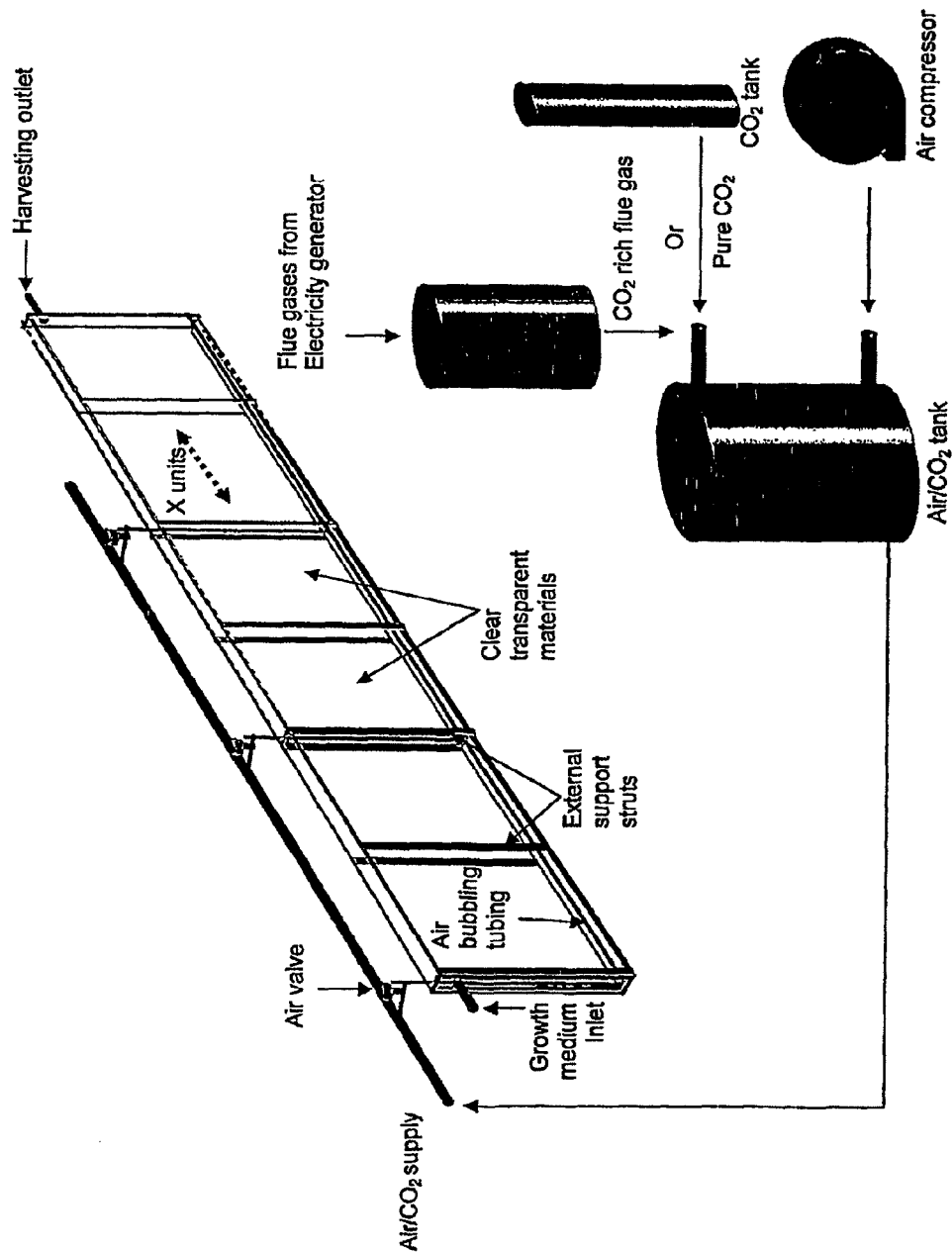
FIG. 8. Aeration system. Pure $CO_2$ or $CO_2$-rich flue gas can be blended with air at a certain ratio to facilitate culture mixing while providing carbon source for algal photosynthesis.

The photobioreactors of this first aspect of the invention also comprise an aeration system in fluid communication with the container. The aeration system comprises any suitable system for (a) introducing a carbon dioxide supply into the container; and (b) introducing compressed air to effect culture mixing. Such an aeration system may comprise, for example, air tubing made of flexible, or rigid plastic (such as silicon or PVC tubing), or metal (such as stainless steel). For example, aeration can be provided by compressed air passing though perforated tubing running along the container bottom (FIG. 8). In case that reactor sidewalls are quite high (for example, 6 feet or higher), a second aeration line may be introduced, for example, halfway between the top and bottom of the reactor to enhance culture mixing. Holes of certain diameter (preferably between 0.1~2.0 mm) set certain distance (preferably 10~50 mm) (from one another along the tubing provide air bubbles to effect culture mixing. Carbon dioxide can be blended with compressed air at a certain percentage (preferably from 0.1% up to 20% of $CO_2$) to provide carbon source for algal photosynthesis. In some cases, organic carbon (for example, in the form of acetic acid and/or glucose) can be added as needed into the culture medium to support algal growth. Any suitable source of carbon dioxide can be used, including but not limited to industrial grade, food grade, $CO_2$-rich flue gases emitted from power generators burning coal, biomass (including algal biomass and/or biomass residues after high-value products are extracted), natural gas, biogas (e.g., ethanol, methane obtained from anaerobic digestion/fermentation of algal biomass or biomass residues and/or from anaerobic digestion of wastewater), and liquid fossil fuel or biofuels (including algae-based biodiesel).

Figure 3:
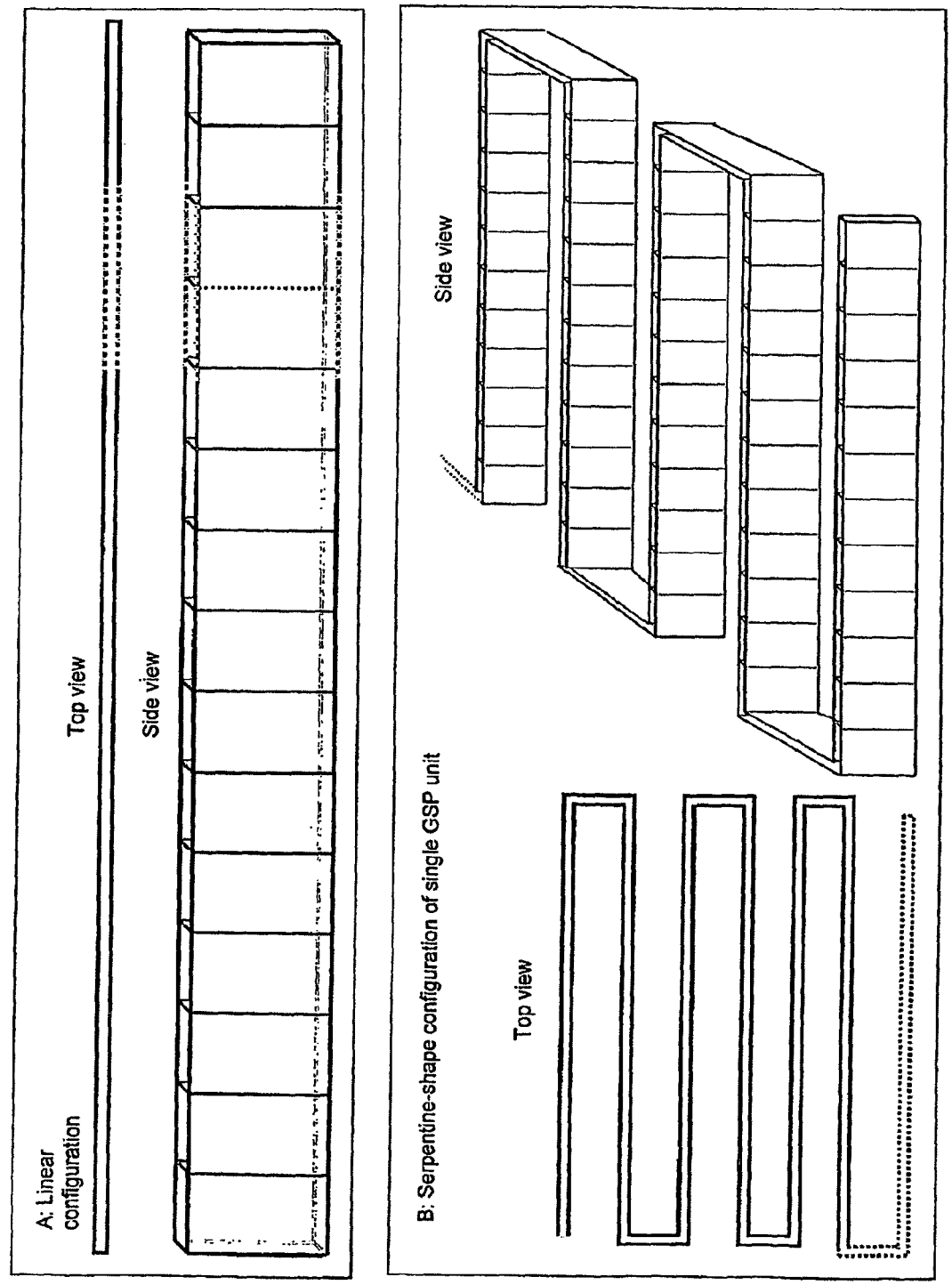
FIG. 3. Examples of configuration of single reactor unit with a linear and serpentine-shape are presented.

The photobioreactors of the first and second aspects of the invention can be linear or serpentine in shape; see, for example, FIG. 3.

In a further embodiment of this first aspect, the photobioreactor further comprises at least one drainage outlet. In a preferred embodiment, a drainage outlet is located in an endwall opposite the inlet port, and near the bottom of the endwall. As discussed above, when an over-flow mode is used for harvesting, then, the drainage has a separate port, preferably close or at the bottom of the reactor to facilitate draining of water/culture with minimum energy requirement. Normally, there will be a single drainage outlet per reactor unit. However, for a reactor unit of extended length, multiple drainage outlets may be preferred. For instance, for a serpentine-shape reactor unit, drainage ports may be located at individual endwall sides.

Figure 2:
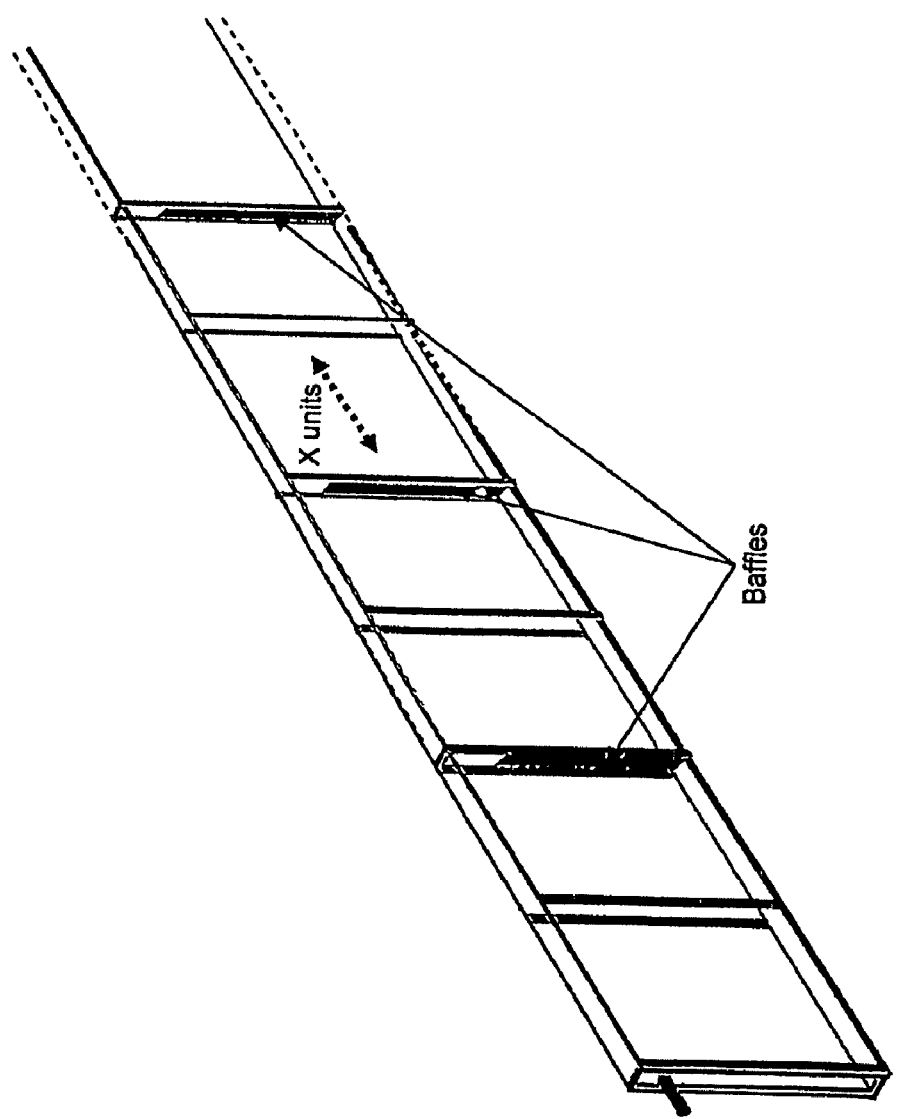
FIG. 2. A reactor unit with multiple compartments partially separated by baffles.

In a further embodiment of this first aspect, the container further comprises one or more baffles connected to the first and second sidewalls, so as to form a barrier and to partially separate the container into multiple compartments. Baffles are especially preferred in embodiments where the sidewalls are long (for example, 10 to 1,000 meters long) to partially separate the container into multiple compartments. The baffles are designed such that they allow the upper portion of individual compartments to open to one another. While the baffle can be of any height desired by a user, it is preferred that the baffle height is between 60% and 90%, and more preferably between 70% and 80% of the height of the sidewalls. When such baffles are used, culture suspension in individual compartments can flow from one compartment to another, although the lower parts of individual compartments are isolated (FIG. 2). The purpose of such design is that in case one particular compartment is broken, the rest of the container compartments will still hold most of the culture suspension.

Figure 20A:
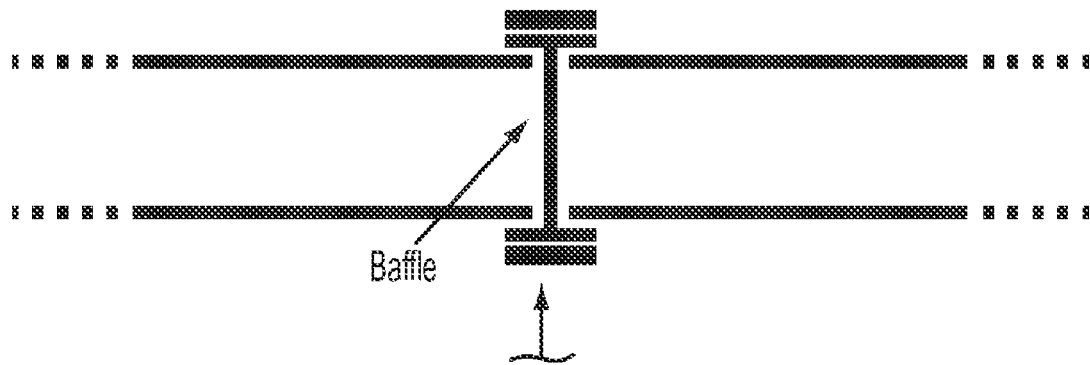
FIG. 20. Top—(A) and side-views (B) of baffle-mounting strut. The baffle can be made of, for example, metal, glass, or high-strength plastic sheet.
Figure 20B:
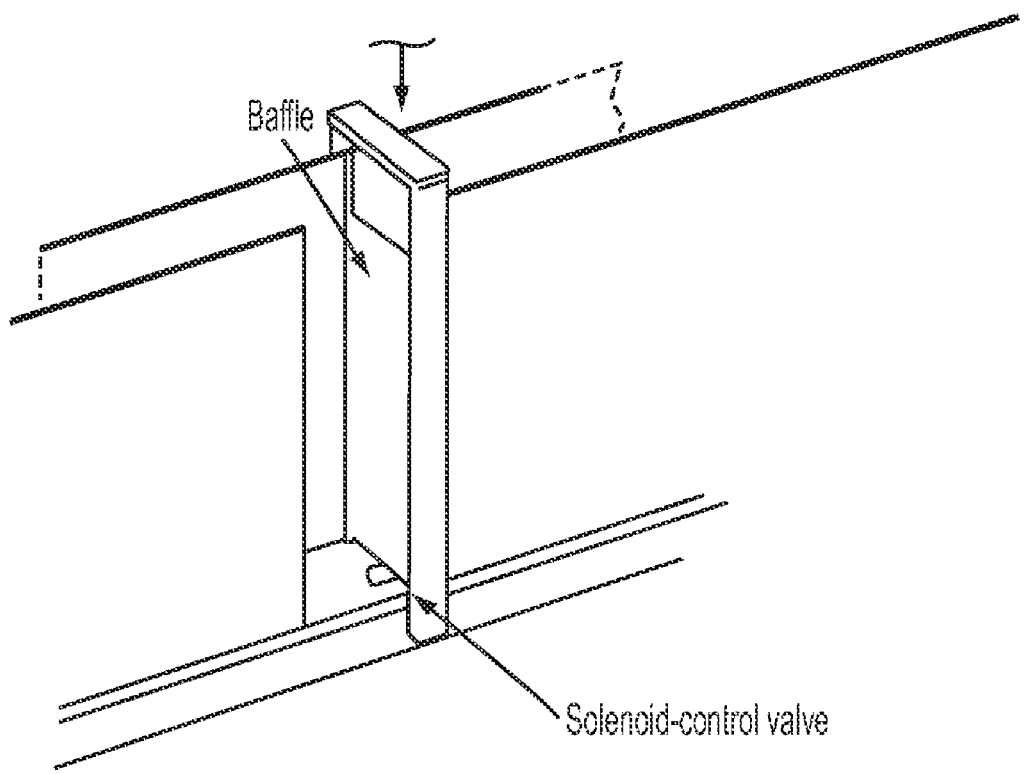

The baffle can be made of any material suitable for inclusion in a container supporting algal growth, including but not limited to glass, stainless steel plate, and rigid plastic sheet. In general, the materials used for one or both sidewalls and/or end walls can be used for baffle structure as well. The thickness of the baffle depends on the type and mechanical strength of materials, and height of the baffle. For a strut where a baffle is joined, the strut provides not only the surface for sidewalls to join, but also the surface on which the baffle is mounted. Both the side- and lower-edge of the baffle can be joined to the strut frame to create separation of individual compartments at the lower section, leaving the upper section open to enable culture suspensions in individual compartments to communicate and mix. In one embodiment, a solenoid-controlled valve is located at or near the bottom of the baffle, which can open or close as needed (See FIG. 20). When the valve is open, all the compartments within a reactor unit are inter-connected not only via the upper section, but through the valve opening. When the valve is closed, only the upper parts of individual compartments are inter-connected. Under normal conditions, the solenoid valve on the baffle is in the open position. It can be closed, for example, when an accident occurs, (e.g., container leaking, sidewalls broken), or as otherwise desired by the operator.

In one non-limiting example of a photobioreactor according to this first aspect of the invention, a single linear photobioreactor unit is 100 meters long. Nine baffles are inserted equally apart (10 meters distance) from one another to create 10 compartments in the container. The height of the baffles is somewhat shorter than that of sidewalls or struts, cell culture suspensions in all individual compartments are mixed on the top part. The purpose of the baffle structure in the reactor unit is to prevent loss of the entire culture in case one piece of sidewall is broken due to whatever reasons. The amount of culture lost in this case is only from the broken compartment along with a small portion of culture above the height of the baffle structure. It is suggested that an appropriate distance between individual baffles would be 10 to 50 meters. In other words, the reactor compartment created between two baffles should provide an inner space of 5,000 to 100,000 liters.

In another embodiment, the invention provides photobioreactor modules, comprising two or more photobioreactors of the first aspect of the invention, wherein the containers of the photobioreactors are in fluid communication. In this embodiment, the individual photobioreactor containers may in direct fluid communication at the inlet (i.e.: an inlet supplying culture medium, etc. to each of the photobioreactor containers in the module; they may be in fluid communication when set in parallel the fluid from individual photobioreactor containers can be harvested through outlet ports connected to a common harvesting/draining manifold system; a combination thereof, or via some other means of fluid communication between the individual photobioreactor containers.

Figure 7:
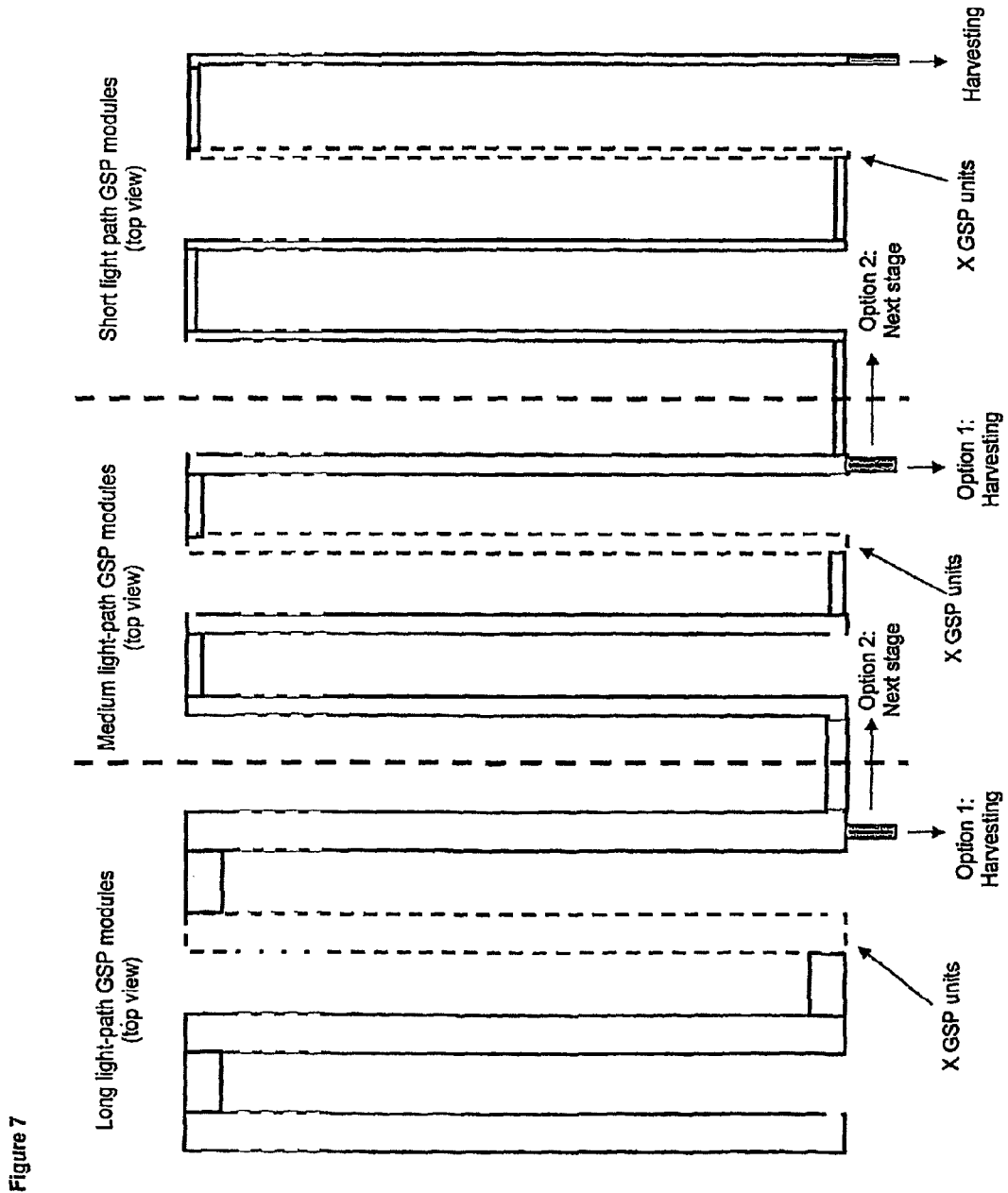
FIG. 7. Examples of reactor modules with various lengths of light paths of reactors.
Figure 13:
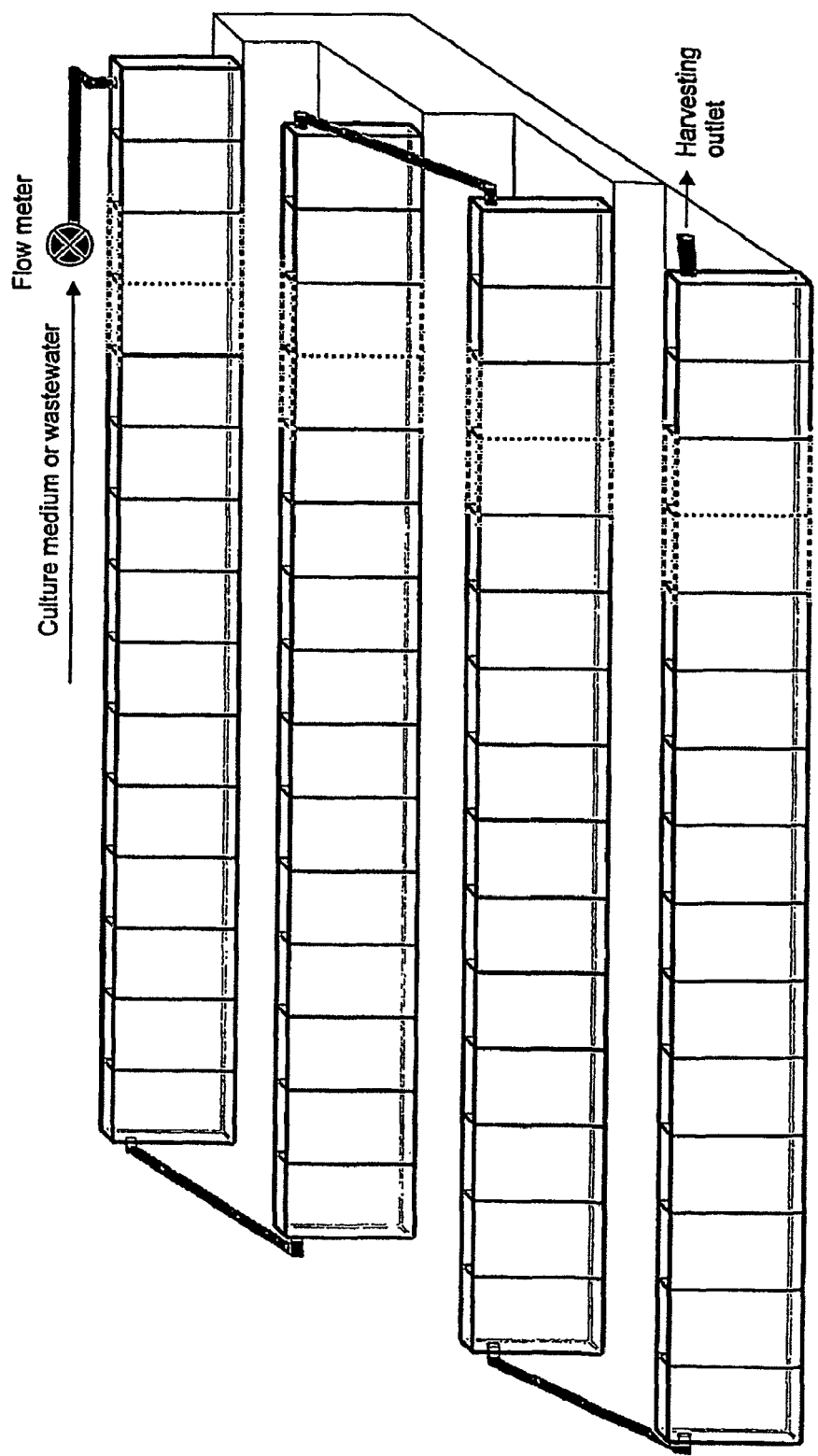
FIG. 13: Reactor units and/or reactor modules can be set up at the same level, or at different levels. In this particular case, the reactor units are set-up in a step-wise fashion.

The two or more photobioreactors in a module may have the same of different light paths. The invention also provides photobioreactor clusters, comprising two or more photobioreactor modules of the invention. The two or more photobioreactor modules in a cluster may also have the same or different light paths. FIG. 7 illustrates an example of a particular reactor cluster in which individual reactor modules vary in the length of the light path. In this case, harvesting of algal suspension can take place at the end of each individual reactor module, or at the end of a cascading, multiple reactor cluster. FIG. 13 shows an example of individual photobioreactors set stepwise so that algal culture can flow down by gravity from the top photobioreactor to the photobioreactor of the lowest level. All photobioreactors, modules thereof, or clusters thereof can also be set up at the same level. FIG. 3 is a case where an individual photobioreactor is set at the same level.

Figure 21:
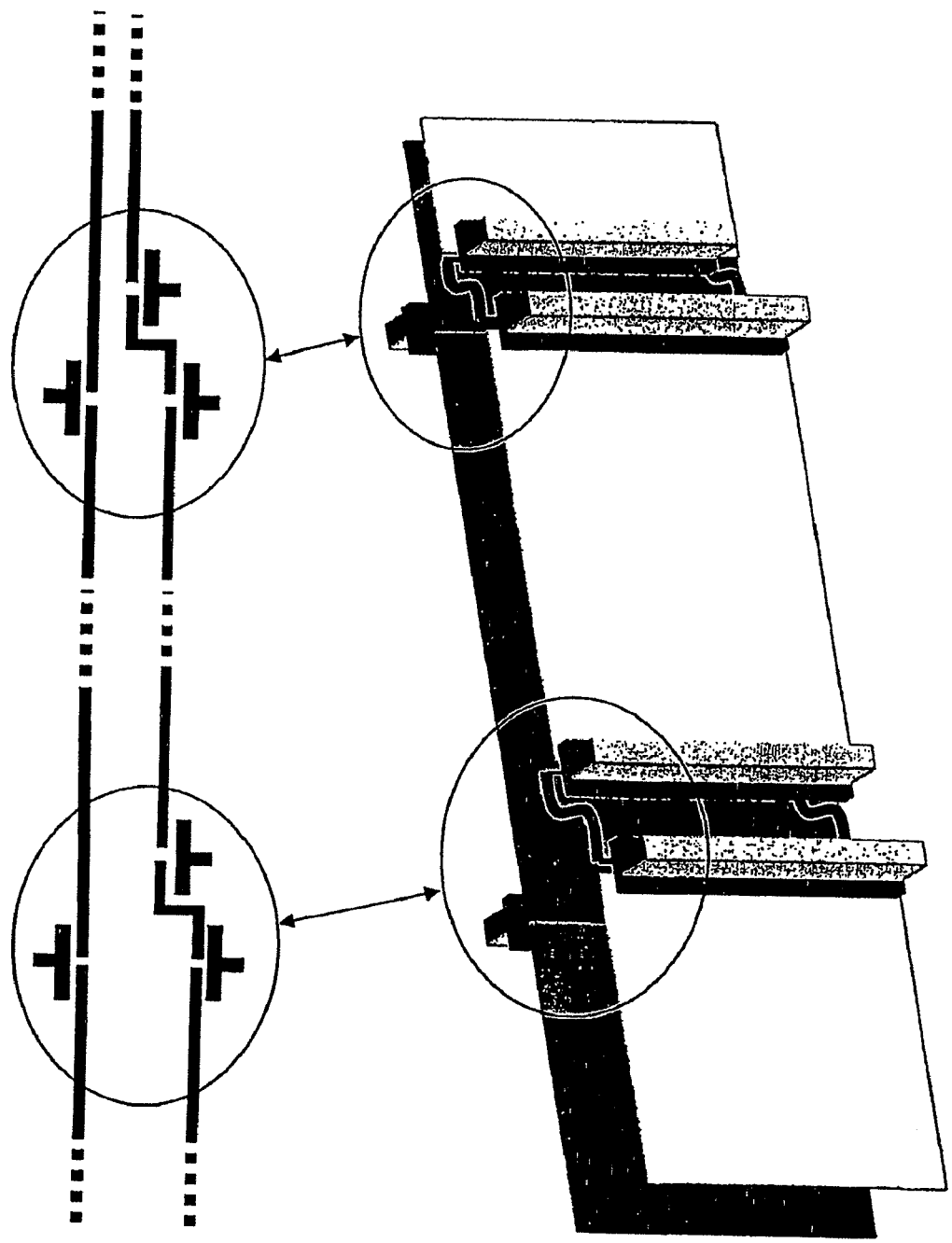
FIG. 21. Top- and side-views of reactor sections where the length of light path changes as desired. The Z-shape connectors can be made of, for example, a plastic sheet (such as PVC) or a metal sheet (such as stainless steel). Such design enables a single reactor unit to have different lengths of light path, as desired.

A photobioreactor "unit" is as described for the first aspect of the invention; i.e.: a single photobioreactor. It can have the same or different lengths of light path along its length, and can be linear or serpentine in shape, and usually it has one or multiple inlets at one end of the reactor, and one or multiple outlets located at the opposite side of the reactor. See FIG. 21 for an example of design to achieve a different light path in a photobioreactor.

The "photobioreactor module" comprises multiple photobioreactor units arranged in parallel. When the reactor units are in a linear configuration, all the inlets of all individual reactor units face one direction, whereas outlets of reactor units face an opposite direction. If reactor units are in a serpentine configuration, all the inlets and outlets may be either at the same or in an opposite direction. In a preferred embodiment, algal cells of the same physiological or nutrient status are maintained within a reactor module.

A "photobioreactor cluster" comprises multiple reactor modules. Individual modules may have the same or different lengths of the light path. Preferably, a culture flows from reactor modules having the largest reactor light path and/or highest nutrient load growth medium to reactor modules of reduced light path to reactor modules of the narrowest light path and nutrient depleted growth medium. The connection of individual reactor modules is flexible, depending on specific algal species/strain and/or production of specific products. For example, a reactor cluster comprising reactor units/modules of large light path will be preferred for production of the high value phycobiliproteins or long-chain polyunsaturated fatty acids from certain cyanobacteria and microalgae. In contrast, to maximize production of neutral lipids and secondary carotenoids, the reactor cluster preferably comprises multiple reactor modules arranged such that the culture flows from reactor modules of large light paths to reactor modules of narrower light paths.

In a second aspect, the present invention provides a photobioreactor panel unit, comprising:

(a) a container adapted for holding fluid, comprising opposing first and second sidewalls and opposing first and second endwalls, wherein the container define an interior, a top opening and a bottom opening, wherein at least one of the first and second sidewalls is transparent, and wherein the first and second sidewalls are substantially flat;

(b) a top cap that fits over the top opening of the panel body; and (c) a base cap that fits under the bottom opening of the panel body;

one or both of the top cap and the bottom cap further comprise one or more channels, to provide fluid connection to a separate photobioreactor panel unit.

The photobioreactor panel unit of this second aspect of the invention is a single unit that can be connected together via the channels to form a multi-unit photobioreactor module, as described below. As such, it provides for scale up of flat plat-type design to a commercial level, and thus fulfills a great need in the art.

In a preferred embodiment of this second aspect, the container, the base cap, and the top cap are plastic, and the photobioreactor panel unit is made using plastic extrusion technology, where the plastic is pushed and/or drawn through a die to create long objects with a fixed cross-section. Hollow sections can be formed, for example, by placing a pin or mandrel in the die. Extrusion may be continuous to produce indefinitely long materias, or semi-continuous, to repeatedly produce multiple shorter pieces.

The advantage of plastic extrusion technology is to enable mass production of standard reactor units at considerably reduced price. The standard sizes of reactor units will also enable simple, quick assembling of reactor units into modules or arrays. This method will also increase the height of the reactors potentially to 10 to 20 meters in height, thereby reducing the number of reactor units and thus reducing captical/maintenance costs.

The first and second sidewalls of this second aspect of the invention, and various embodiments thereof, are similar to those described in the first aspect of the invention.

Figure 5:
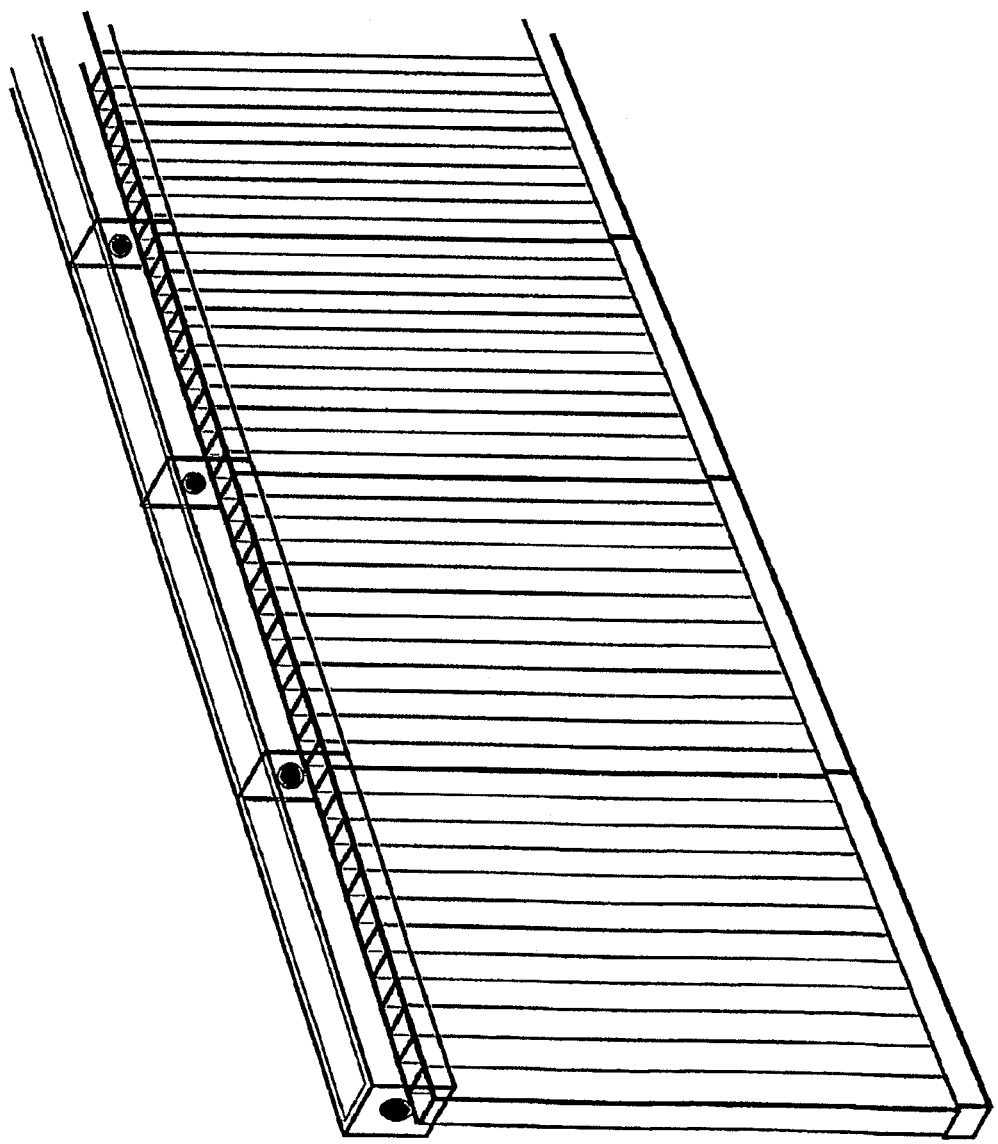
FIG. 5. Another geometric configuration of the reactor consisting of multiple reactor units. Culture suspension in individual units is connected through both top- and base-cap structures.

The top-cap fits over the top opening of the panel body to prevent airborne-dusts/microbial organisms from entering the culture, prevent water evaporation, release air and excess oxygen generated through algal photosynthesis, and to connect individual panels one another side by side. For example, the top cap shown in FIG. 5 actually comprises multiple individual top caps joined to one another. Both base and top caps are designed such that they can be readily connected for added length as desired. Thus, algal culture suspensions in individual flat-panel units can mix and flow from one panel to another (FIG. 5). The bottom cap fits under the bottom opening of the panel body, to provide integrity to the panel body for holding fluid, and thus the capability to serve as an algal photobioreactor.

Embodiments of the top cap and the bottom cap are similar to those described above for the container bottom and top.

In this second aspect, one or both of the top cap and the bottom cap further comprise one or more channels, to provide fluid connection to a separate photobioreactor panel unit, to allow culture suspension to flow from one individual panel to another. In a preferred embodiment, the one or more channels are present in the top cap.

Figure 4:
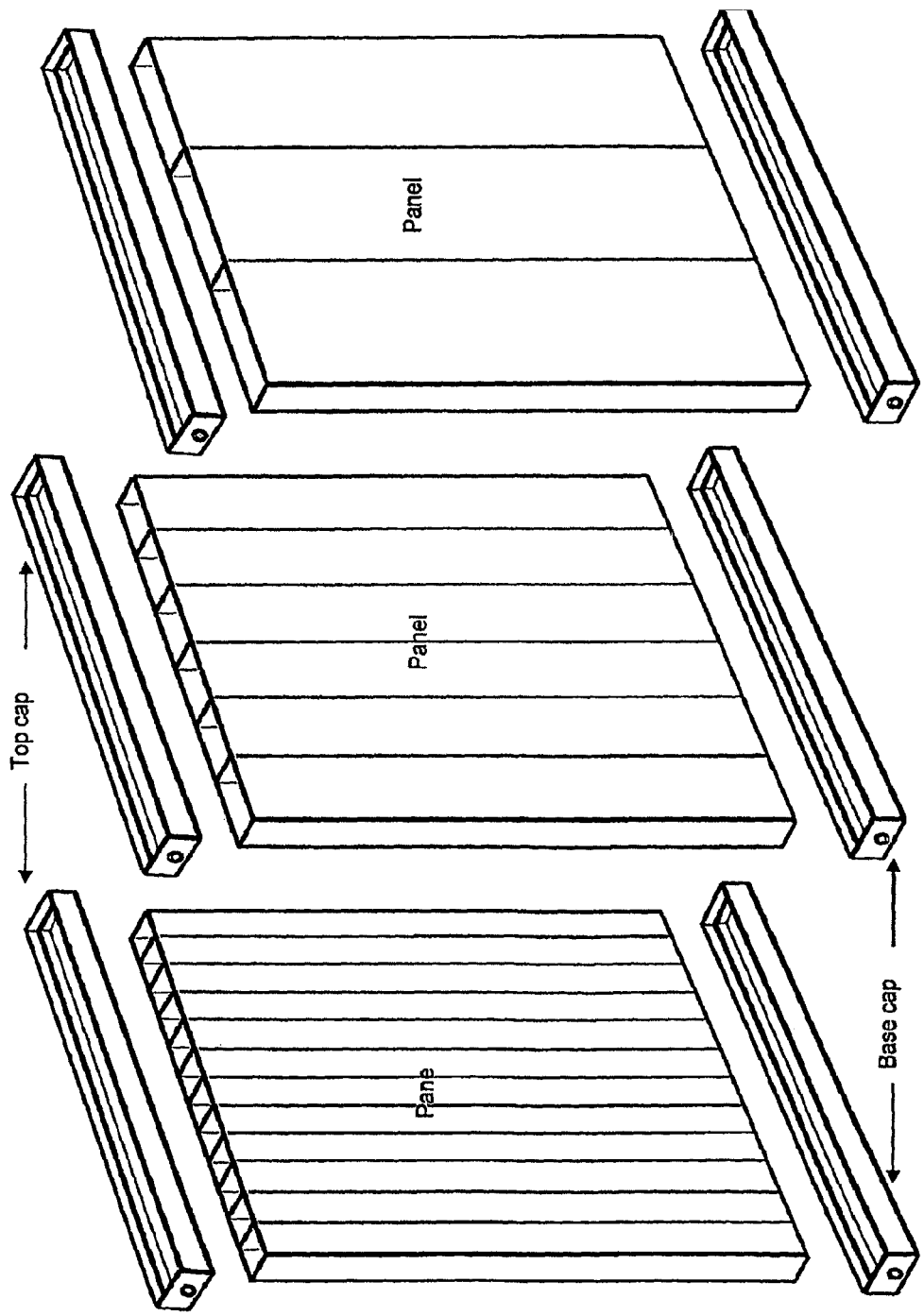
FIG. 4. Another geometric configuration of the reactor. reactor units can be made using plastic extrusion technology. A reactor unit consists of three parts: body panel, and top- and base-caps.

In a preferred embodiment of this second aspect, the interior comprises one or more baffles extending between the first and second sidewalls, so that the interior comprises a plurality of compartments. The distance between baffles can be variable based on a user's specific needs, as shown in FIG. 4. Baffles and embodiments thereof are as described above for the first aspect of the invention.

In another preferred embodiment, the base cap further comprises an aeration system, as disclosed above for the first aspect of the invention. In a preferred embodiment, the aeration system comprises air-bubble tubing inserted along the bottom of the base cap to provide aeration to affect culture mixing and provide carbon dioxide supply. Aeration systems and embodiments thereof are as described above for the first aspect of the invention.

In another preferred embodiment, one or both of the top cap and bottom cap further comprise an inlet port in fluid communication with the interior, for introducing fluid, including but not limited to culture medium, algal suspensions, and nutrient solutions, into the interior of the photobioreactor panel unit. In a preferred embodiment, the inlet port is located in the top cap. It will be understood that, where multiple photobioreactor panel units of this second aspect are connected, that only one such inlet port is required, and thus not all individual units need to comprise such a port. However, any or all of the individual units may comprise an inlet port. Inlet ports and preferred embodiments thereof are as described above for the first aspect of the invention.

In another preferred embodiment of this second aspect, one or both of the top cap and bottom cap further comprise at least one outlet port in fluid communication with the interior, for removing fluid from the container, including algal culture suspensions for harvesting. In a preferred embodiment, the outlet port is located in the top cap. It will be understood that, where multiple photobioreactor panel of this second aspect are connected, that only one such inlet port is required, and thus not all individual units need to comprise such a port. However, any or all of the individual units may comprise an inlet port. Outlet ports and preferred embodiments thereof are as described above for the first aspect of the invention.

In a further embodiment of this first aspect, at least one of the top cap and bottom cap further comprise at least one drainage outlet. In a preferred embodiment, a drainage outlet is located in the bottom cap. Drainage ports and preferred embodiments thereof are as described above for the first aspect of the invention.

Figure 6:
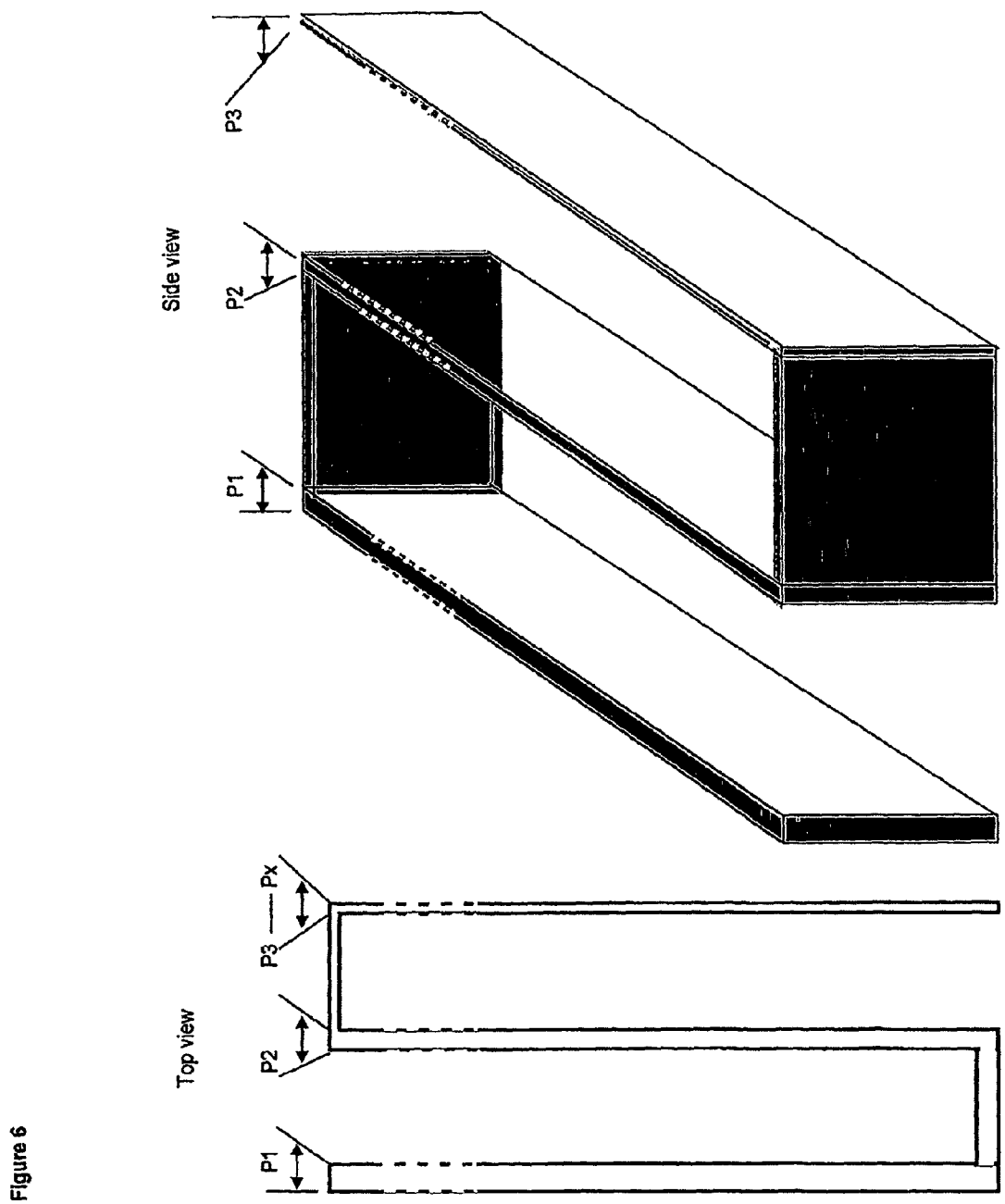
FIG. 6. Examples of single reactor unit with various lengths of light path (P1, P2, P3, and Px) represent different lengths of light paths of reactors.

The following embodiments apply to either or both of the first and second aspects of the invention. In one further embodiment, the distance between the first and second sidewalls varies at different locations in the photobioreactor. As discussed above, the distance between the inner face of the first and second sidewalls constitutes the light path of the photobioreactor. In this embodiment, the photobioreactor can have an equal length of either long or narrow light paths, or vary in light path along the horizontal axis, i.e., having a long light path at one end, and gradually reducing the length of light path while moving towards the opposite end of the photobioreactor. An example of a photobioreactor with different distances between the first and second side walls (i.e.: different light paths) is shown in FIG. 6.

Such variable light paths can be used, for example, with specific algal strains to be cultured and/or specific desirable end-products (e.g., high-value carotenoids, total lipids, and proteins) to be produced at different locations within the photobioreactor, as discussed above and as is known in the art (Hu et al., Biotechnology and Bioengineering 51: 51-60 (1996); Hu et al., European Journal of Phycology 33: 165-171 (1998). In one non-limiting example, a photobioreactor has a light path of 100 mm at one end and a light path of 20 cm at the other end; any type of desirable variation can be employed, as will be apparent to those of skill in the art based on the teachings herein.

Figure 9:
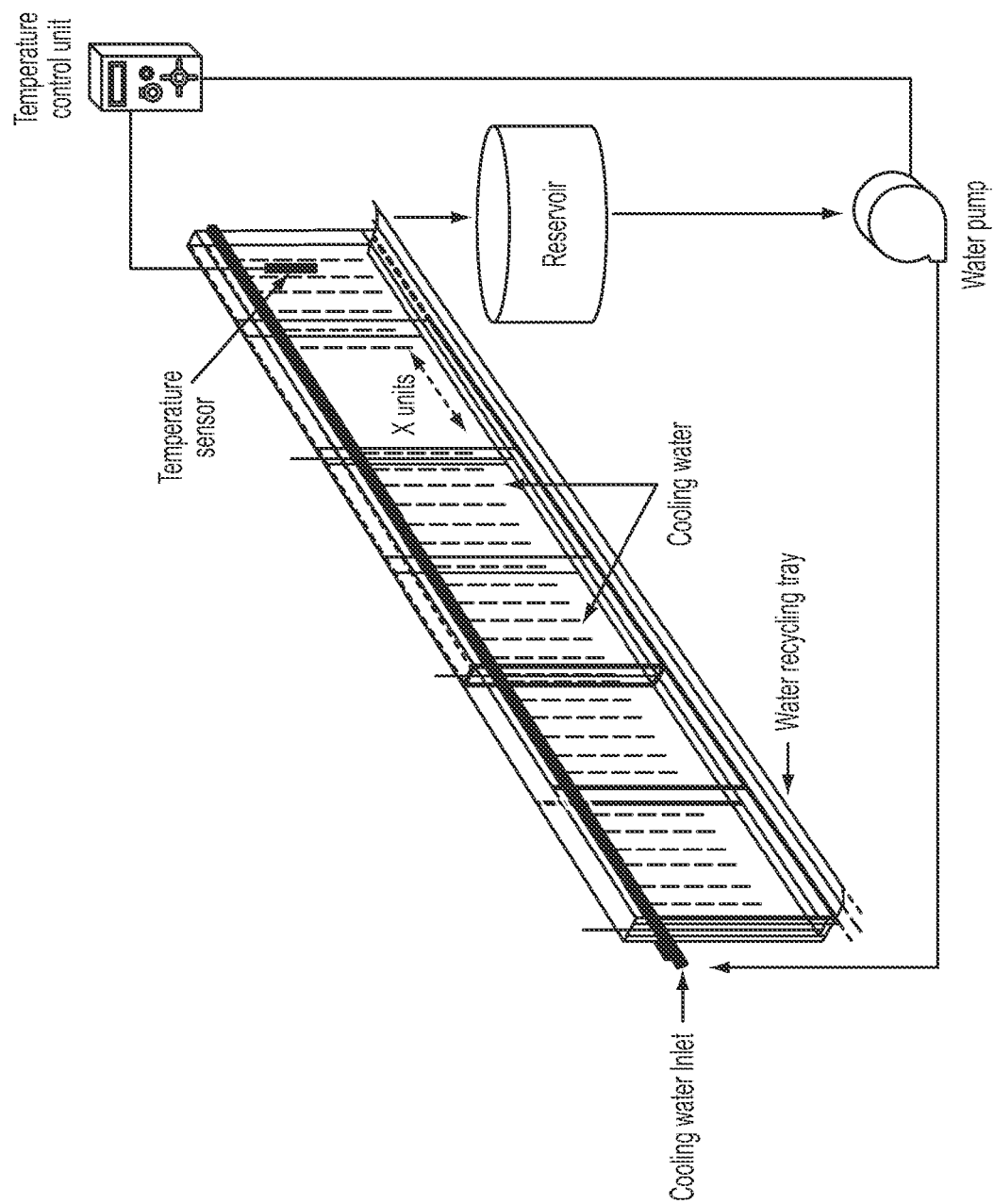
FIG. 9. Evaporative cooling option. The reactor can be maintained at optimal culture temperatures during the summer or when temperature is above the optimal temperature range by evaporative cooling.

In a further embodiment of the first or second aspect, the photobioreactor further comprises a temperature control system. Any suitable temperature control system can be used. One exemplary approach is the application of external temperature control (FIG. 9). Water of a certain temperature from near the top of one side of the reactor can flow down against the external surface (i.e.: the outside face of one or both of the sidewalls) to maintain a desirable internal temperature level for algal growth or specific cellular metabolism. In some embodiments, only the sidewall facing the sun is cooled. For example, one or more water pipes can be placed at or near the bottom of sun-facing side of the reactor. A series of water-spray heads can be fixed at a certain angle to the water pipe, from which tempered water can be sprayed onto the sun-facing surface of the reactor. In a preferred embodiment, the photobioreactor with this type of temperature control system would further comprise a water tray underneath the base cap or container bottom, to collect the cooling water. In a further preferred embodiment, the external temperature control system comprises a pipe that collects water from a reservoir; the water tray subsequently returns the water to the reservoir, where the water temperature can be either increased or decreased as necessary for water recycling.

Figure 10:
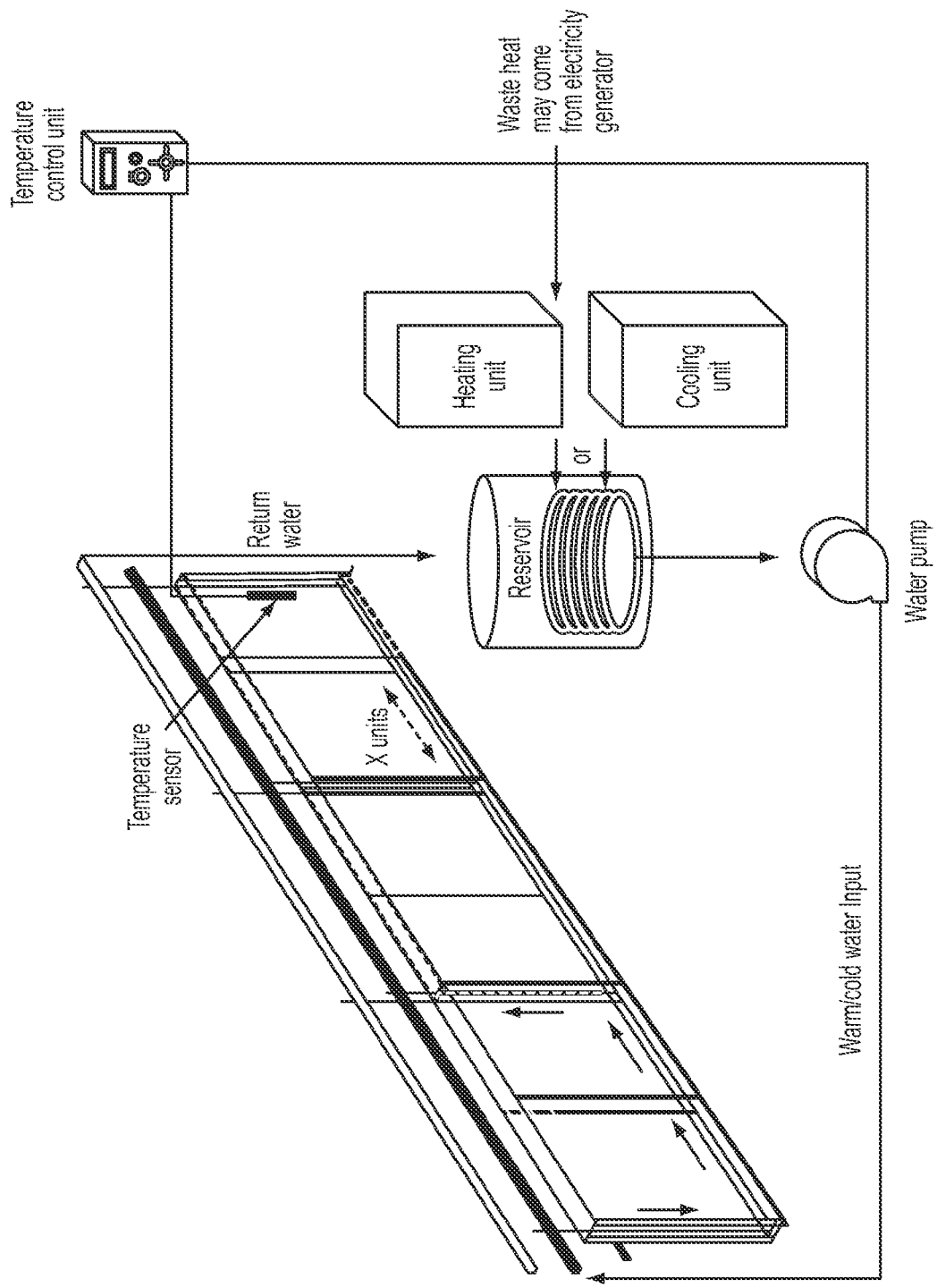
FIG. 10. Internal temperature control option. An optimal culture temperature can be also maintained in the reactor by an internal temperature control system. Metal tubing is inserted into reactor units, in which warm or cold water is circulating to effect culture temperature. Waste heat from power generator burning algal residue or algae-derived biogas can be used to maintain culture temperature during the winter season, or whenever a higher temperature is desirable.

An alternative temperature control system comprises internal temperature control, in which tubing, preferably metal tubing (since metal materials in general have higher heat transfer efficiency than plastic or glass), preferably running along the bottom of the photobioreactor through which temperature-regulated water is circulated to maintain the culture temperature at a desirable level (FIG. 10).

In a further embodiment, the temperature control system comprises a temperature controlled compressed air source. The culture suspension is aerated with temperature-controlled compressed air. In this embodiment, a temperature control element is embedded into the air container to warm or cool compressed air. The cooling element can be a refrigeration unit, an evaporative cooling unit, or equivalents thereof. The heating element can be a commercially available product, or a unit that can utilize waste heat generated from power generators.

In various further embodiments of the first and second aspects of the invention, the photobioreactor further comprises systems and sensors for control of culture pH, $NO_3^-$/$PO_4^{3-}$ levels, and $O_2$ and $CO_2$ concentrations. For example, a monitoring system can be acquired from Aquatic Eco-System, Inc. (Apopka, Fla. 32703).

Figure 11:
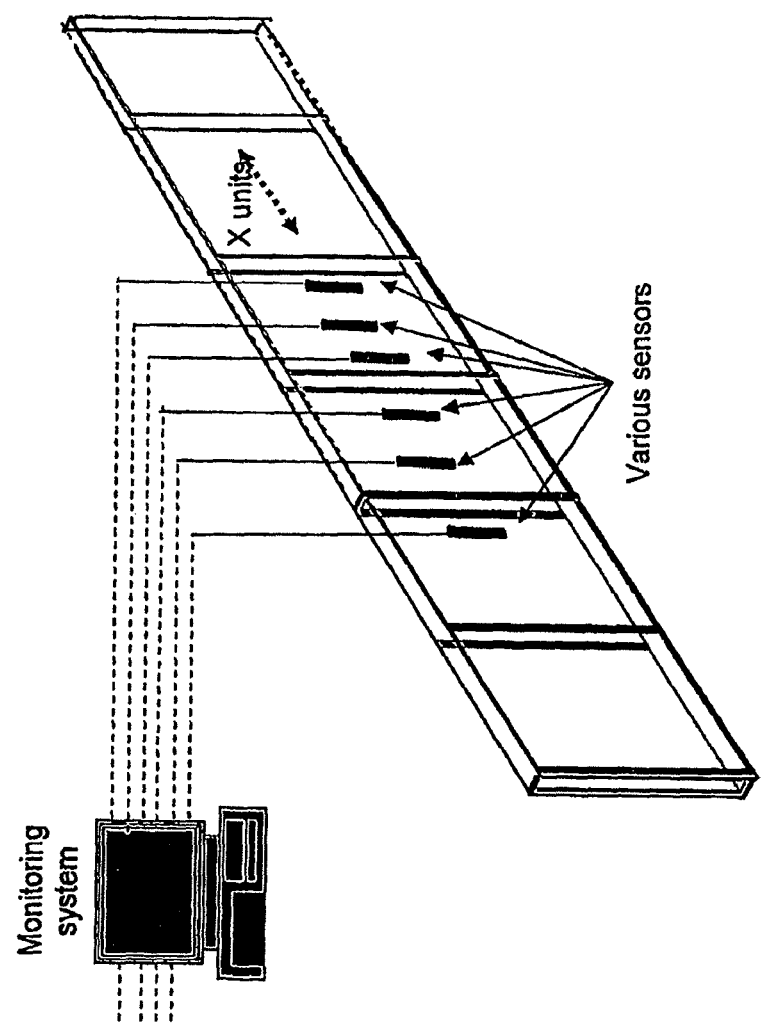
FIG. 11. A computer-based monitoring system is integrated into reactor units and/or modules to monitor and regulate culture pH, temperature, $NO_3^-/PO_4^{-3}$ levels, and $O_2$ and $CO_2$ concentrations. As an integrated component of algal harvesting system, optical-density sensors are inserted into selected reactor units in a reactor module for on-line monitoring of algal cell density and that, in turn, will be used to control algal harvesting.

Any of these control systems and sensors can be implemented using an automatic control system and methodology. In a preferred embodiment, a computer-based monitoring system is integrated into the photobioreactor and/or modules thereof, to monitor and regulate culture pH, temperature, $NO_3^-$/$PO_4^{3-}$ levels, $O_2$ and $CO_2$ concentrations. As an integrated component of algal harvesting system, optical-density sensors can also be inserted into selected photobioreactor units in a module for on-line monitoring of algal cell density, which in turn will be used to control algal harvesting (FIG. 11).

In a further embodiment of the first and second aspects of the invention, the photobioreactor further comprises a means to effect inclination of the photobioreactor. A direct relationship between solar energy and productivity is observed: the higher the amount of solar energy that is admitted by varying the reactor tilt angle according to season, the higher the productivity sustained in the culture. The reactor tilt angle exerts a significant effect on the optimal population density and thus on the productivity of cell mass, due to its effect on the amount of solar radiation impinging on the surface of the reactor.

Figure 12:
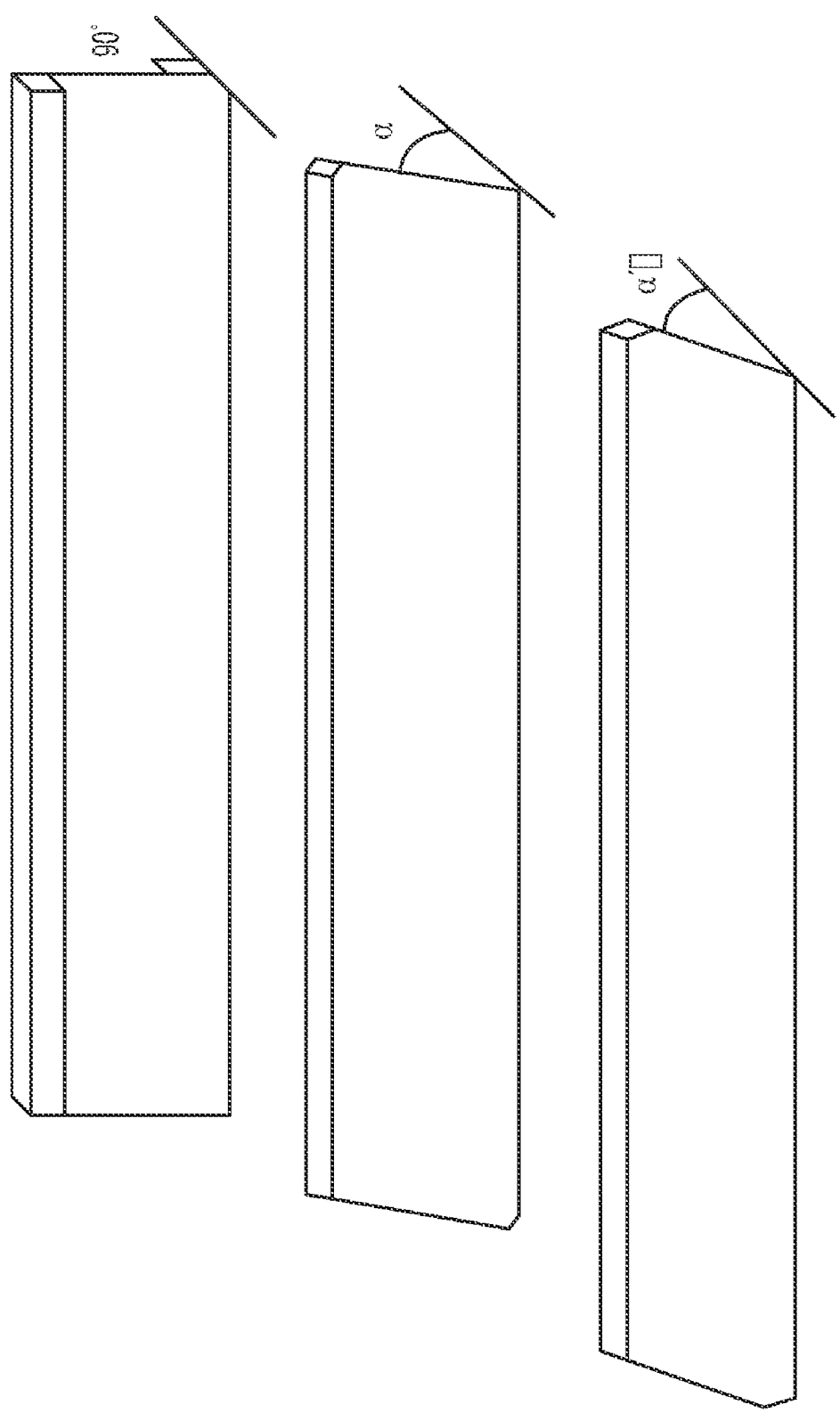
FIG. 12. Inclination of a reactor relative to sun's radiation.

For a given seasonal temperature, biomass productivity depends on the amount of solar radiation admitted to the photobioreactor. Generally, for an equator-facing, one-sided photobioreactor, the optimal tilt angle for maximal year-round energy collection is a tilt angle approximately equal to geographic latitude. The effect of photobioreactor orientation becomes more significant the higher the geographic latitude since the availability of sunlight is more limited than it is closer to the equator. Small tilt angles of 10° to 30° in summer and larger angles in the vicinity of 60° in winter result in maximal productivities for these seasons (FIG. 12).

A benefit in orientating and tilting reactors at various angles to the sun both daily and throughout the year is to reap the maximal potential associated with the biological conversion of solar energy. Studying the effect of the frequency of optimizing the tilt angle on overall annual productivity shows that frequent adjustment for the optimal reactor angle throughout the year will result in the highest overall annual productivity. A potential benefit in orientating and tilting photobioreactors at various appropriate angles to the sun on a seasonal basis: up to 40% enhancement in annual biomass yield can be achievable. From a practical standpoint, adjusting the tilt angle twice a year would significantly enhance overall productivity. This is particularly true for production sites located at higher latitudes.

Any means for effecting inclination of the photobioreactor can be used, such as those disclosed in Hu et al. Journal of Fermentation and Biotechnology 85: 230-236 (1998). In another embodiment, the photobioreactors of the invention can be placed on a berm, such as a mound or bank of earth, that is raised and sized to provide the appropriate inclination of the photobioreactor relative to the sun. In this embodiment, the sidewall facing the berm does not have to be transparent. In this embodiment, the berm may also serve to insulate and help to maintain suitable culture temperatures in the photobioreactor.

To a large range of geographic latitudes, the photobioreactors should be placed in a south-facing orientation to receive maximum solar radiation. However, for certain geographic latitudes (such as Israel), vertical east/west-facing photobioreactors can receive more solar input during summer months than even the most optimally tilted south-facing reactors. Systematic use of our equation enables the optimal configuration of reactors to be identified for any geographic latitude, permitting the relative benefits of east-west orientation to be assessed.

Figure 14:
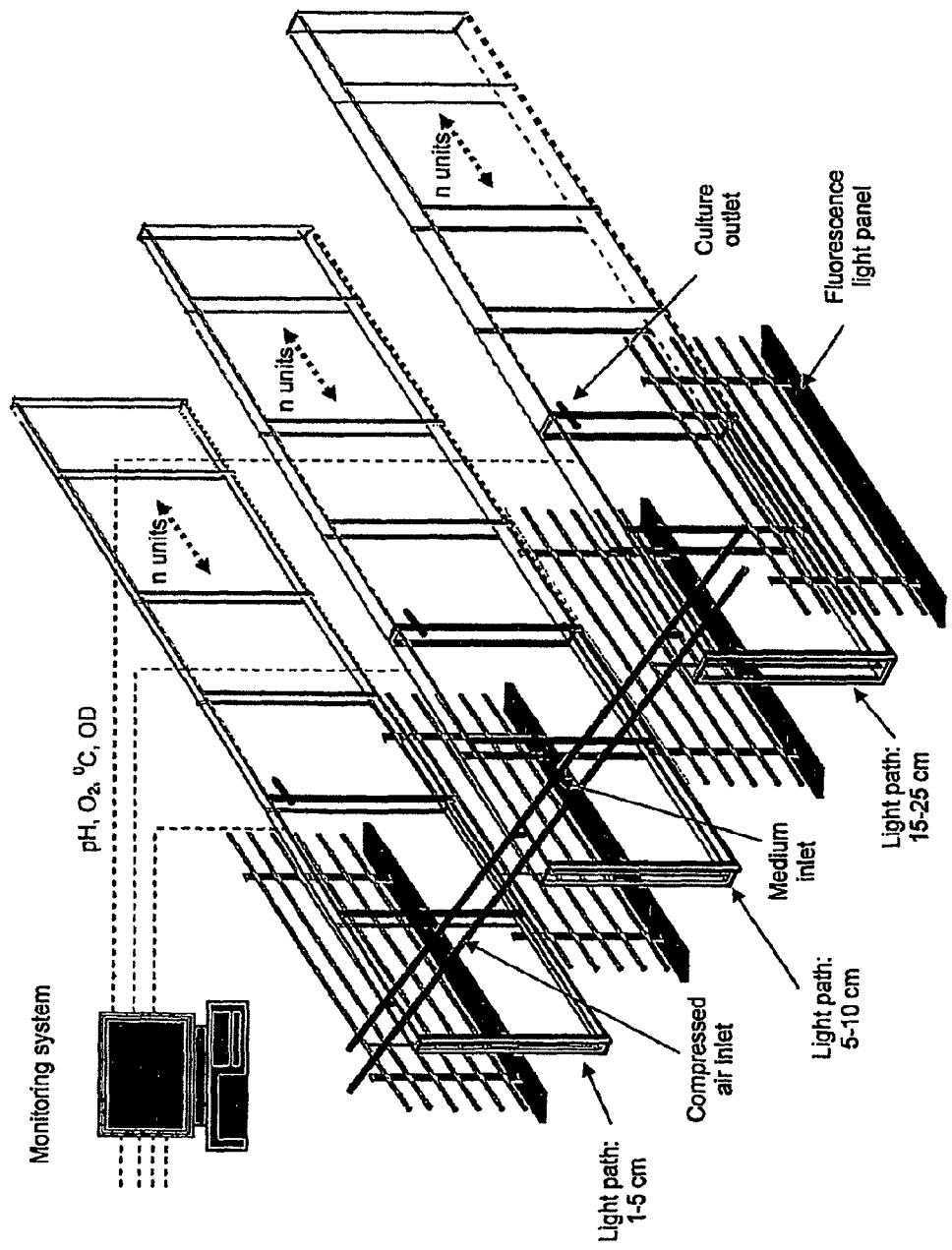
FIG. 14. Schematic diagram of an indoor reactor. Reactor sections in solid lines represent a single unit. Sections with dash-lines indicate potential extension of individual reactor unit to any desired length. Individual reactor units can be connected in cascade and direction of culture flow from larger light-path units to narrower light-path units, or visa versa.

In certain embodiments, the photobioreactors can be used for indoor algal cultures. In this case, artificial illumination can be provided, and one particular source of light is fluorescence tubes (FIG. 14) The only difference between indoor and outdoor reactors of this design is the source of light. The reactors themselves can be identical.

Figure 15:
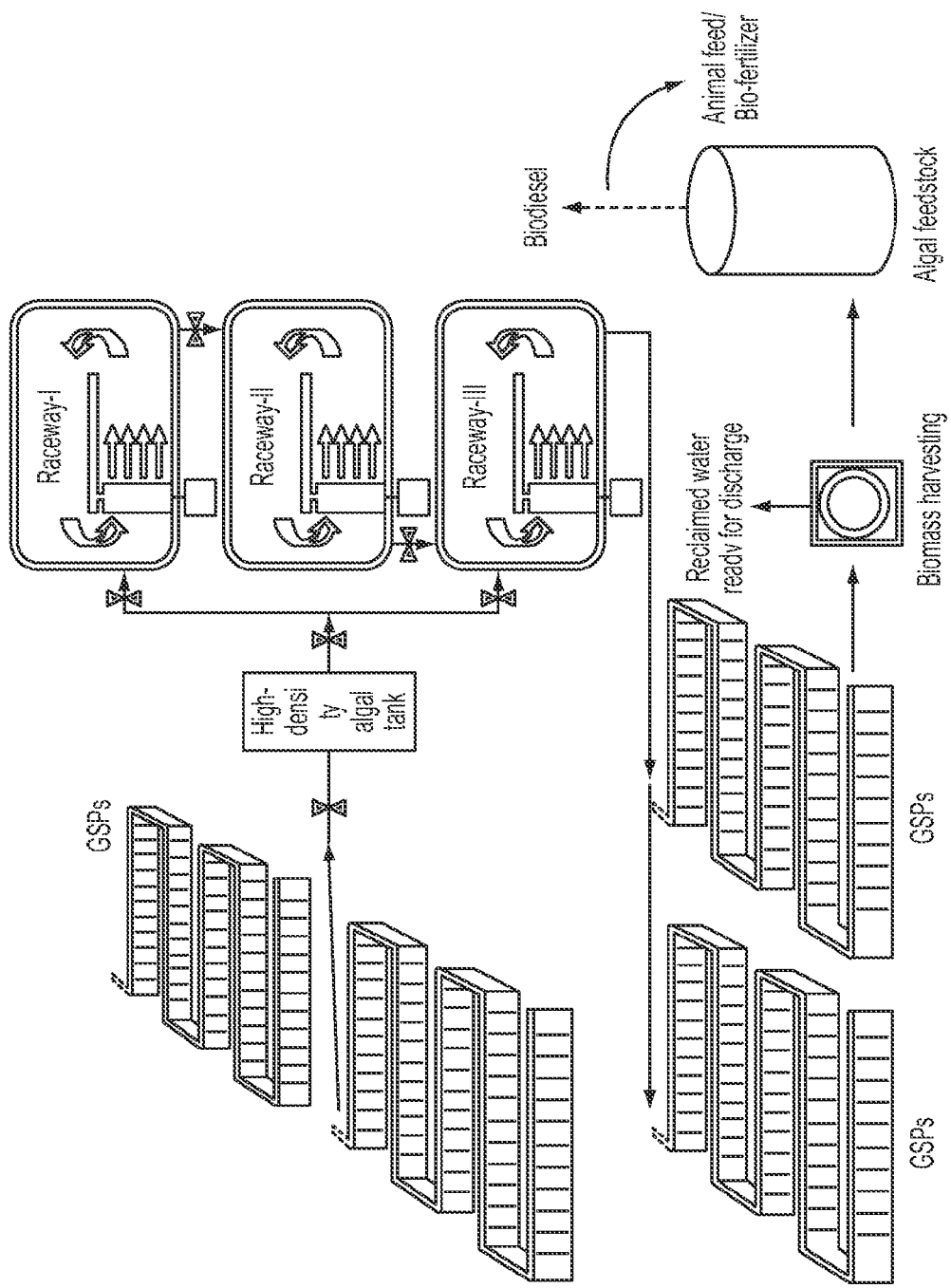
FIG. 15. A hybrid open pond-closed reactor systems. While open ponds serve multi-functions a) as a waste holding pond; b) initial algal adaptation to the field environment; and c) initial nutrient removal and biomass production stages, the closed reactor will i) provide seed culture to the open raceway; ii) polish wastewater to completely remove nutrients from the wastewater; iii) enhance biomass production; and iv) induce cellular accumulation of desirable products (such as high-value pigments, lipids/oil, proteins, or polysaccharides).

In a further embodiment, the photobioreactor of the first and/or second aspect of the invention can be used in combination with an open pond system (FIG. 15). While the open pond will serve multi-functions a) as a waste holding pond; b) initial algal adaptation to the field environment; and c) initial nutrient removal and biomass production stages, the closed photobioreactors of the invention can be used to i) provide seed culture to the open raceway; ii) polish wastewater to completely remove nutrients from the wastewater; iii) enhance biomass production; and iv) induce cellular accumulation of desirable products (such as high-value pigments, lipids/oil, proteins, or polysaccharides).

The photobioreactor of the first or second aspect of the invention can be made as complete individual reactors or modules thereof in a manufacturing site and shipped to a reactor application site for installation and operation, can be made and shipped as separate parts to the application site for assembly and operation, or can be made on-site near or within the reactor application site.

Thus, in a third aspect, the present invention provides methods for making the photobioreactors of the first or second aspect of the invention, comprising assembling the photobioreactor of the first or second aspect of the invention from their component parts. Such component parts will be apparent to those of skill in the art, based on the discussion above of the first and second aspects of the invention.

In a first embodiment, the method comprises assembling a photobioreactor by assembling a container adapted for holding fluid with support struts, wherein the container comprises:

(a) opposing first and second sidewalls, wherein at least one of the first and second sidewalls is transparent;

(b) opposing first and second endwalls;

(c) a container bottom; and (d) a container cover, wherein the first and second sidewalls comprise a plurality of separate sections, and wherein the separate sections are in fluid communication; and wherein the support struts are assembled to connect the plurality of separate sections of the first and second sidewalls.

In exemplary preferred embodiments of this first embodiment, the photobioreactor further comprises at least one inlet port in fluid communication with the container; at least one outlet port in fluid communication with container; an aeration system in fluid communication with the container; and a temperature control system connected to the container so as to control temperature of fluid within the container. The methods can further comprise adding other embodiments of the photobioreactors as described above in the first and second embodiments of the invention.

In a fourth aspect, the present invention provides methods for algae growth, particularly microalgae, comprising culturing algae in the photobioreactor of the first or second aspects of the invention, in the presence of nutrient sources and light, preferably sunlight. Microalgae (for short, algae) are microplants and require mostly simple mineral nutrients for growth and reproduction. By utilizing photon energy, such as sunlight and artificial illumination, algae convert, through photosynthesis, water and carbon dioxide into high-value organic compounds (e.g., pigments, proteins, fatty acids, and secondary metabolites). Accompanied by photosynthesis, nitrogen and phosphorous in wastewater are also taken up and assimilated in algal cells. Algae exhibit a growth potential an order of magnitude greater than higher plants because of their extraordinarily efficient light and nutrient utilization.

Nutrient sources for such algal growth include, but are not limited to, standard algal culture media, animal wastewater, wastewater from concentrated animal feeding operations, nutrient contaminated groundwater and/or agriculture runoff water can be used as growth medium after balancing with certain chemicals, including but not limited to phosphate and trace elements, underground saline water after spiked with certain chemicals, including but not limited to nitrate and phosphate, industrial wastewater, domestic wastewater, and contaminated groundwater, as well as waste gases emitted from power generators that burn algal biomass residues after desired products are extracted and recovered, flue gas emissions from fossil fuel fired power plants, dairy wastewater containing high concentrations of ammonia and phosphate, groundwater of high nitrate levels.

As discussed above, the use of different nutrient concentrations affect the growth and biochemical composition of algal cells. For example, nutrient-rich medium may stimulate and sustain a high growth rate and biomass productivity, whereas nutrient depleted medium may stimulate biosynthesis and cellular accumulation of neutral lipids, long chain fatty acids, and/or secondary carotenoids. A nutrient gradient created in a photobioreactor of the first or second aspects of the invention thus allows a continuous shifting of algae from a high biomass production mode to a high accumulation of specific desired product mode.

In a preferred embodiment for use in the methods of this fourth aspect of the invention, the photobioreactors of the first or second aspect are used and are placed on a berm, such as a mound or bank of earth, that is raised and sized to provide the appropriate inclination of the photobioreactor relative to the sun for maximum harvesting of solar radiation, as discussed above.

This fourth aspect further comprises methods for harvesting algal cells from culture suspension maintained in the photobioreactors of the invention, using various approaches (e.g., centrifugation, dissolved air flotation, or membrane filtration). Industrial preparative centrifuges of several kinds can be used to harvest algal cells from the photobioreactors. These methods can be used to produce high-value algal products, such as long chain unsaturated fatty acids, carotenoids, phycobiliproteins, chlorophyll, and polysaccharides. A dissolved air flotation method for harvesting algal cells from a reactor can also be used. (Hoffland Environmental, Inc. Silver Springs Road, Conroe Tex. 77303-1602; SAMCO Technologies, Inc. 160 Wales Avenue, PO Box 906, Tonawanda, N.Y. 14150) Such method is particularly useful in a process where treatment of wastestream (such as waste nutrients and $CO_2$) is coupled with algal biomass production. A membrane filtration can also be used to harvest algal cells. (e.g., US Membranes Corp.)

The methods of this fourth aspect of the invention can be used for a variety of purposes, including but not limited to production of algae-derived products (pharmaceuticals, nutraceuticals, agrochemicals, human food, and animal feed); production of recombinant proteins; environmental remediation, including but not limited to removal and recycling of waste nutrients from wastewater and carbon dioxide-rich flue gases emitted from fossil fuel-fired power generators; and production of algal biomass for use as feedstock and for production of biofuels (such as biodiesel, ethanol, or methane), animal feed additives, and organic fertilizers.

Those of skill in the art are familiar with standard algal culture methods in photobioreactors. See, for example, Gitelson et al., Applied and Environmental Microbiology 62: 1570-1573 (1996); Hu and Richmond (1994) Journal of Applied Phycology 6: 391-396; Hu et al., (1998) Journal of Fermentation and Biotechnology 85: 230-236; Hu et al., (1996) Biotechnology and Bioengineering 51: 51-60; Hu et al., (1996) Journal of Phycology 32: 1066-1073; Hu et al., (1998) Applied Microbiology and Biotechnology 49: 655-662; Hu et al., (1998) European Journal of Phycology 33: 165-171; and Hu, *Industrial production of microalgal cellmass and secondary products—major industrial species: Arthrospira (Spirulina) platensis*. Pp. 264-272. In: Richmond A. (ed.) Handbook of microalgal culture: biotechnology and applied Phycology, Blackwell Science Ltd., Oxford, UK.

REFERENCES CITED

Chaumont D. (1993) Biotechnology of algal biomass production: a review of systems for outdoor mass culture. J Appl Phycol 5: 593-604

Chaumont D., Thepenier C. and Gudin C. (1988) Scaling up a tubular photobioreactor for continuous culture of *Porphyridium cruentum*—from laboratory to pilot plant, pp. 199-208. In Stadler T, Morillon J, Verdus M S, Karamanos W, Morvan H, Christiaen D (eds.), *Algal Biotechnology*, Elsevier Applied Science, London.

Cornwell, D. A. (1990). Air Stripping and Aeration, in Water Quality and Treatment, McGraw Hill Inc., New York, pg. 229-268.

Fernandez, F. G., Camacho, F. G., Perez, J. A., Sevilla, J. M., Grima, E. M. (1998). Modeling of biomass productivity in tubular photobioreactors for microalgal cultures: effects of diluation rate, tube diameter, and solar irradiance, *Biotech. And Bioeng.*, 58:6:605-616.

Gitelson A., Hu Q. and Richmond A. (1996) Photic volume in photobioreactors supporting ultrahigh population densities of the photoautotroph *Spirulina platensis*. Applied and Environmental Microbiology 62: 1570-1573.

Gudin C. and Chaumont D. (1991) Cell fragility—the key problem of microalgae mass production in closed photobioreactors. *Bioresource Technol*. 38: 145-151.

Hu Q. and Richmond A. (1994) Optimizing the population density of *Isochrysis galbana* grown outdoors in a glass column photobioreactor. Journal of Applied Phycology 6: 391-396.

Hu Q., Faiman D. and Richmond A. (1998a) Optimal orientation of enclosed reactors for growing photoautotrophic microorganisms outdoors. Journal of Fermentation and Biotechnology 85: 230-236.

Hu Q., Guterman H. and Richmond A. (1996a) A flat inclined modular photobioreactor (FIMP) for outdoor mass cultivation of photoautotrophs. Biotechnology and Bioengineering 51: 51-60.

Hu Q., Guterman H. and Richmond A. (1996b) Physiological characteristics of *Spirulina platensis* cultured at ultrahigh cell densities. Journal of Phycology 32: 1066-1073.

Hu Q., Kurano N., Iwasaki I., Kawachi M. and Miyachi S. (1998b) Ultrahigh cell density culture of a marine green alga, *Chlorococcum littorale* in a flat plate photobioreactor. Applied Microbiology and Biotechnology 49: 655-662.

Hu Q., Yair Z. and Richmond A. (1998c) Combined effects of light intensity, light-path and culture density on output rate of *Spirulina platensis* (Cyanobacteria). European Journal of Phycology 33: 165-171.

Hu Q. 2004. Industrial production of microalgal cell-mass and secondary products—major industrial species: *Arthrospira* (*Spirulina*) *platensis*. Pp. 264-272. In: Richmond A. (ed.) Handbook of microalgal culture: biotechnology and applied Phycology, Blackwell Science Ltd., Oxford, UK.

Iwasaki I., Hu Q., Kurano N. and Miyachi S. (1988) Effect of extremely high-$CO_2$ stress on energy distribution between photosystem I and photosystem II in a 'High-$CO_2$' tolerant green alga, *Chlorococcum littorale* and the intolerant green Alga *Stichococcus bacillaris*. Journal of Photochemistry and Photobiology B: Biology 44/3: 184-190.

Lee Y. K. (1986) Enclosed bioreactor for the mass cultivation of photosynthetic microorganism: the future trend. *Trends Biotechnol.* 4: 186-189.

Lee Y. K., Ding S. Y., Low C. S. and Chang Y. C. (1995) Design and performance of an α-type tubular photobioreactor for mass cultivation of microalgae. J. Appl. Phycol 7:47-51

Pirt S. J., Lee Y. K., Walach M. R., Pirt M. W., Balyuzi H. H. M. and Bazin M. J. (1983) A tubular bioreactor for photosynthetic production of biomass from carbon dioxide: design and performance. *J. Chem. Tech. Biotechnol*. 33: 35-58.

Ramos de Ortega and Roux J. C. (1986) Production of *Chlorella* biomass in different types of flat bioreactors in temperate zones. *Biomass* 10: 141-156.

Richmond A. (1990) Large scale microalgal culture and applications. In: Round/Chapman (eds) Progress in Phycological Research Biopress, London, 7: 1-62

Richmond A. (1992) Open systems for mass production of photoautotrophic microalgae outdoors: physiological principles. *J. Appl. Phycol.* 4: 281-286

Richmond A. and Hu Q. (1997) Principles for utilization of light for mass production of photoautotrophic microorganisms. Applied Biochemistry and Biotechnology. 63-65: 649-658.

Richmond A., Boussiba S., Vonshak A. and Kopel R. (1993) A new tubular reactor for mass production of microalgae outdoors. *J. Appl. Phycol.* 5: 327-332.

Samson R & Leduy A (1985) Multistage continuous cultivation of blue-green alga *Spirulina maxima* in the flat tank photobioreactors with recycle. *Can. J. Chem. Eng.* 63: 105-112.

Silva, H. J., Cortinas T. and Ertola R. J. 1987. Effect of hydrodynamic stress on Dunaliella growth. *J. Chem. Tech. Biotechnol.* 40: 253-264.

Tamiya H. (1957) Mass culture of algae. *Ann Rev. Plant Physiol.* 8: 309-334.

Torzillo G., Carlozzi P., Pusharaj B., Montani E. and Materassi R. (1994) A two-plane tubular photobioreactor for outdoor culture of *Spirulina. Biotechnol. Bioeng.* 42: 891-898.

Tredici M. R. and Materassi R. (1992) From open ponds to vertical alveolar panels: the Italian experience in the development of reactors for the mass cultivation of photoautotrophic microorganisms. *J. Appl. Phycol.* 4: 221-31.

Tredici M. R., Carlozzi P., Zittelli G. C. and Materassi R. (1991) A vertical alveolar panel (VAP) for outdoor mass cultivation of microalgae and Cyanobacteria. *Bioresource Technol.* 38: 153-159.

Tredici M. (2004) Mass production of microalgae: photobioreactors, pp. 178-214. In: Richmond A. (ed.) Handbook of microalgal culture: biotechnology and applied Phycology, Blackwell Science Ltd., Oxford, UK.

Watanabe Y., Joel de la Noue. And Hall D. O. (1995) Photosynthetic performance of a helical tubular photobioreactor incorporating the cyanobacterium *Spirulina platensis*. Biotechnol Bioeng 47: 261-269

Xiu, Z-L, Zeng, A-P, Deckwer, W-D (1998). Multiplicity and stability analysis of microorganisms in continuous culture: effects of metabolic overflow and growth inhibition, *Biotechnology and Bioeng.*, 57:3:251-261.

We claim:

1. A method for algae growth, comprising the steps of:
   (I) incubating algae in a growth medium in a photobioreactor comprising,
      (a) a container adapted for holding fluid, comprising
         (i) opposing first and second sidewalls, wherein at least one of the first and second sidewalls is transparent;
         (ii) opposing first and second endwalls;
         (iii) a container bottom; and
         (iv) a container cover,
         wherein the first and second sidewalls comprise a plurality of separate sections, and wherein the separate sections are in fluid communication;
      (b) support struts for connecting the plurality of separate sections of the first and second sidewalls, wherein the support struts are located entirely on the exterior of the container;
      (c) at least one inlet port in fluid communication with the container;
      (d) at least one outlet port in fluid communication with the container;
      (e) an aeration system in fluid communication with the container; and (f) a temperature control system connected to the container so as to control temperature of fluid within the container; and (II) exposing the algae to light.

2. The method of algae growth of claim 1 wherein the photobioreactor further comprises a pH control system.

3. The method of algae growth of claim 1 wherein the photobioreactor further comprises a $NO_3^-/PO_4^{3-}$ level control system.

4. The method of algae growth of claim 1 wherein the photobioreactor further comprises an $O_2$ level control system.

5. The method of algae growth of claim 1 wherein the photobioreactor further comprises a $CO_2$ level control system.

* * * * *